United States Patent
Moon

(10) Patent No.: US 7,217,712 B2
(45) Date of Patent: May 15, 2007

(54) 4-SUBSTITUTED-5-CYANO-1H-PYRIMIDIN-6-(THI)ONES AS GSK-3 INHIBITORS

(75) Inventor: Young-Choon Moon, Belle Mead, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/799,507

(22) Filed: Mar. 12, 2004

(65) Prior Publication Data

US 2004/0186119 A1 Sep. 23, 2004

Related U.S. Application Data

(60) Provisional application No. 60/454,878, filed on Mar. 12, 2003.

(51) Int. Cl.
*C07D 239/36* (2006.01)
*C07D 239/56* (2006.01)
*C07D 405/04* (2006.01)
*A61K 31/513* (2006.01)

(52) U.S. Cl. .................. 514/235.8; 514/269; 544/122; 544/123; 544/319

(58) Field of Classification Search ................ 544/122, 544/123, 319; 514/235.8, 269
See application file for complete search history.

(56) References Cited

FOREIGN PATENT DOCUMENTS

| | | |
|---|---|---|
| EP | 1 074 549 | 11/2003 |
| WO | WO 01/70728 | 9/2001 |
| WO | WO 02/096905 | 12/2002 |

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Casanova et al., PubMed Abstract (Rev Neurol 28(9):909-15), May 1999.*
Hardt et al., Glycogen Synthase Kinase-3beta., Circulation Research, 90:1055-1063, May 2002.*
Mittelbach et al., CAPLUS Abstract 92:146395, 1980.*
Abdel-Megid et al., CAPLUS Abstract 139:36510, 2003.*
Abdel-Megid, CAPLUS Abstract 133:30702, 2000.*
Kobayashi et al., CAPLUS Abstract 88:31980, 1978.*
Gary W. Cline et al, "Effects of a Novel Glycogen Synthase Kinase-3 Inhibitor on Insulin-Stimulated Glucose Metabolism in Zucker Diabetic Fatty(fa/fa) Rats", Diabetes, 51: 2903-2910 (2002).
Erik J. Henriksen et al, "Modulation of Muscle Insulin Resistance by Selective Inhibition of GSK-3 in Zucker Diabetic Fatty Rats", American Journal of Physiology Endocrinology and Metabolism, 284: E892-E900 (2003).

\* cited by examiner

*Primary Examiner*—Deepak Rao
(74) *Attorney, Agent, or Firm*—Jennifer G. Che; Lisa A. Dixon

(57) ABSTRACT

The present invention relates to compounds of formula I that are useful as GSK-3 inhibitors. The invention also relates to methods of using compounds of formula I or pharmaceutical compositions comprising compounds of formula I to inhibit GSK-3 activity. The invention further provides methods of utilizing these compounds and pharmaceutical compositions in the treatment and prevention of various GSK-3-mediated disorders, such as diabetes and Alzheimer's disease.

21 Claims, No Drawings

US 7,217,712 B2

4-SUBSTITUTED-5-CYANO-1H-PYRIMIDIN-6-(THI)ONES AS GSK-3 INHIBITORS

CROSS REFERENCE TO RELATED APPLICATIONS

This application claims priority to U.S. Provisional Patent Application 60/454,878, filed Mar. 12, 2003, the content of which is incorporated by reference.

TECHNICAL FIELD OF THE INVENTION

The present invention relates to compounds useful as inhibitors of glycogen synthase kinase-3. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. See, Hardie, G. and Hanks, S. *The Protein Kinase Facts Book, I and II*, Academic Press, San Diego, Calif.: 1995. Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576–596; Knighton et al., *Science* 1991, 253, 407–414; Hiles et al., *Cell* 1992, 70, 419–429; Kunz et al., *Cell* 1993, 73, 585–596; Garcia-Bustos et al., *EMBO J.* 1994, 13, 2352–2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor $\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of $\alpha$ and $\beta$ isoforms that are each encoded by distinct genes [Coghlan et al., *Chemistry & Biology* 2000, 7, 793–803; and Kim and Kimmel, *Curr. Opinion Genetics Dev.*, 2000 10, 508–514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117–130]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor $\beta$-catenin, the translation initiation factor e1F2B, as well as ATP citrate lyase, axin, heat shock factor-1, c-Jun, c-myc, c-myb, CREB, and CEPB$\alpha$. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455–8459; Cross et al., *Biochem. J.* 1994, 303, 21–26); Cohen, *Biochem. Soc. Trans.* 1993, 21, 555–567; and Massillon et al., *Biochem J.* 1994, 299, 123–128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known $\beta$-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 1994, 4, 1077–86; and Brownlees et al., *Neuroreport* 1997, 8, 3251–55]. Therefore, GSK-3 activity may promote generation of the neurofibrillary tangles and the progression of Alzheimer's disease.

Another substrate of GSK-3 is $\beta$-catenin, which is degradated after phosphorylation by GSK-3. Reduced levels of $\beta$-catenin have been reported in schizophrenic patients and have also been associated with other diseases related to increase in neuronal cell death [Zhong et al., *Nature* 1998, 395, 698–702; Takashima et al., *PNAS* 1993, 90, 7789–93; and Pei et al., *J. Neuropathol. Exp* 1997, 56, 70–78].

GSK-3 activity has also been associated with stroke [Wang et al., *Brain Res* 2000, 859, 381–5; Sasaki et al., *Neurol Res* 2001, 23, 588–92; Hashimoto et al., *J. Biol. Chem* 2002, 277, 32985–32991].

Accordingly, there is a great need to develop compounds useful as inhibitors of protein kinases. In particular, it would be desirable to develop compounds that are useful as inhibitors of glycogen synthase kinases (e.g., GSK-3), particularly given the inadequate treatments currently available for the majority of the disorders implicated in their activation.

SUMMARY OF THE INVENTION

It has now been found that compounds of this invention and pharmaceutically compositions thereof, are effective as inhibitors of glycogen synthase kinase-3. These compounds have the general formula I:

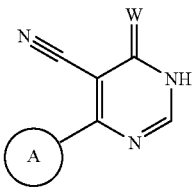

I or a pharmaceutically acceptable salt thereof, wherein W and ring A are as defined below.

These compounds and pharmaceutically acceptable compositions thereof are useful for treating or preventing a variety of diseases, disorders or conditions, including, but not limited to, heart diseases, immunodeficiency disorders, inflammatory diseases, allergic diseases, asthma, autoimmune diseases, immunologically-mediated diseases, neurodegenerative or neurological disorders, metabolic disorders, diabetes, Alzheimer's disease, Huntington's disease, Parkinson's disease, multiple sclerosis (MS), neurological and neurodegenerative disorders, AIDS-associated dementia, amyotrophic lateral sclerosis (AML, Lou Gehrig's disease), schizophrenia, cardiomyocyte hypertrophy, reperfusion/ischemia, stroke, or baldness.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Compounds of the Invention:

The present invention relates to a compound of formula I:

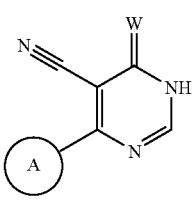

I or a pharmaceutically acceptable, salt thereof, wherein:

W is oxygen or sulfur;

ring A is a 5–6 membered aryl, heterocyclyl or heteroaryl ring having 0–4 heteroatoms independently selected from nitrogen, oxygen, or sulfur;

wherein ring A is optionally substituted with 1–4 groups independently selected from halo, —$R^1$, —$OR^1$, —$SR^1$, —$NO_2$, —CN, —$N(R^1)_2$, —$NR^1C(O)R^1$, —$NR^1C(O)N(R^1)_2$, —$NR^1CO_2R^1$, —$NR^1NR^1C(O)R^1$, —$NR^1NR^1C(O)N(R^1)_2$, —$NR^1NR^1CO_2R^1$, —$C(O)C(O)R^1$, —$C(O)CH_2C(O)R^1$, —$CO_2R^1$, —$C(O)R^1$, —$C(O)N(R^1)_2$, —$OC(O)N(R^1)_2$, —$S(O)_2R^1$, —$SO_2N(R^1)_2$, —$S(O)R^1$, —$NR^1SO_2R^1$, —$NR^1SO_2N(R^1)_2$, —$C(=S)N(R^1)_2$, —$C(=NH)$—$N(R^1)_2$, =O, =S, =$NNHR^1$, =$NN(R^1)_2$, =$NNHC(O)R^1$, =$NNHCO_2(R^1)$, =$NNHSO_2(R^1)$, or =$NR^1$, wherein two independent occurrences of $R^1$, on the same substituent or different substituents, optionally taken together with the atom or atoms to which each $R^1$ group is bound, form a 3–8-membered cycloalkyl, heterocyclyl, aryl, or heteroaryl ring having 0–3 heteroatoms independently selected from nitrogen, oxygen, or sulfur;

each $R^1$ is independently selected from hydrogen, aliphatic, aryl, heteroaryl or heterocyclyl, wherein each member of $R^1$ except hydrogen is optionally substituted with halo, —$R^2$, —$OR^2$, —$SR^2$, —$NO_2$, —CN, —$N(R^2)_2$, —$NR^2C(O)R^2$, —$NR^2C(O)N(R^2)_2$, —$NR^2CO_2R^2$, —$NR^2NR^2C(O)R^2$, —$NR^2NR^2C(O)N(R^2)_2$, —$NR^2NR^2CO_2R^2$, —$C(O)C(O)R^2$, —$C(O)CH_2C(O)R^2$, —$CO_2R^2$, —$C(O)R^2$, —$C(O)N(R^2)_2$, —$OC(O)N(R^2)_2$, —$S(O)_2R^2$, —$SO_2N(R^2)_2$, —$S(O)R^2$, —$NR^2SO_2R^2$, —$NR^2SO_2N(R^2)_2$, —$C(=S)N(R^2)_2$, —$C(=NH)$—$N(R^2)_2$, =O, =S, =$NNHR^2$, =$NN(R^2)_2$, =$NNHC(O)R^2$, =$NNHCO_2(R^2)$, =$NNHSO_2(R^2)$, or =$NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur;

each $R^2$ is independently selected from hydrogen, aliphatic, aryl, heteroaryl or heterocyclyl, wherein each member of $R^1$ except hydrogen is optionally substituted with halo, —$R^3$, —$OR^3$, —$SR^3$, —$NO_2$, —CN, —$N(R^3)_2$, —$NR^3C(O)R^3$, —$NR^3C(O)N(R^3)_2$, —$NR^3CO_2R^3$, —$NR^3NR^3C(O)R^3$, —$NR^3NR^3C(O)N(R^3)_2$, —$NR^3NR^3CO_2R^3$, —$C(O)C(O)R^3$, —$C(O)CH_2C(O)R^3$, —$CO_2R^3$, —$C(O)R^3$, —$C(O)N(R^3)_2$, —$OC(O)N(R^3)_2$, —$S(O)_2R^3$, —$SO_2N(R^3)_2$, —$S(O)R^3$, —$NR^2SO_2R^2$, —$NR^3SO_2N(R^3)_2$, —$C(=S)N(R^3)_2$, —$C(=NH)$—$N(R^3)_2$, =O, =S, =$NNHR^3$, =$NN(R^3)_2$, =$NNHC(O)R^3$, =$NNHCO_2(R^3)$, =$NNHSO_2(R^3)$, or =$NR^3$; and each $R^3$ is independently hydrogen or unsubstituted aliphatic;

provided that when ring A is phenyl, it must be substituted.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.:

Smith, M. B. and March, J., John Wiley & Sons, New York: 2001, the entire contents of which are hereby incorporated by reference.

It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. The term "stable", as used herein, refers to compounds that are not substantially altered when subjected to conditions to allow for their production, detection, recovery, purification, and/or use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic, bicyclic or tricyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic $C_3$–$C_8$ hydrocarbon or bicyclic $C_8$–$C_{12}$ hydrocarbon that is completely saturated or that contains one or more units of unsaturation, but which is not aromatic, that has a single point of attachment to the rest of the molecule wherein any individual ring in said bicyclic ring system has 3–7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or more carbon atoms are independently replaced by a heteroatom. Heteroaliphatic groups may be substituted or unsubstituted, branched or unbranched, cyclic or acyclic, and include "heterocycle", "heterocyclyl", "heterocyclo-aliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, tetrahydrofuranyl, tetrahydrothiophenyl, morpholinoyl, thiomorpholinoyl, pyrrolidinyl, piperazinyl, piperidinyl, thiazolidinyl, aziranyl, oxiranyl, azetidinyl, pyrrolinyl, dioxolanyl, imidazolinyl, imidazolidinyl, pyrazolinyl, pyrazolidinyl, pyranyl, dioxanyl, dithianyl, trithianyl, quinuclidinyl, oxepanyl, and thiepanyl.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$(as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" or "halo" means F, Cl, Br, or I.

The term "aryl" used alone or as part of a larger moiety as in "aralkyl", "aralkoxy", or "aryloxyalkyl", refers to monocyclic, bicyclic, or tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aralkyl" refers to an alkyl group substituted with an aryl group. The term "aralkoxy" refers to an alkoxy group substituted with an aryl group. The term "aryloxyalkyl" refers to an alkyl group substituted with an —O-aryl group.

Examples of aryl groups include, but are not limited to, phenyl, naphthyl, anthracyl, indanyl, phenanthridinyl, and tetrahydronaphthyl.

The term "heteroaryl", used alone or as part of a larger moiety as in "heteroaralkyl" or "heteroarylalkoxy", refers to monocyclic, bicyclic, or tricyclic ring systems having a total of five to fourteen ring members, wherein at least one ring in the system is aromatic, at least one ring in the system contains one or more heteroatoms, and wherein each ring in the system contains 3 to 7 ring members. One having ordinary skill in the art will recognize that the maximum number of heteroatoms in a stable, chemically feasible heteroaryl ring is determined by the size of the ring and valence. The term "heteroaryl" may be used interchangeably with the term "heteroaryl ring" or the term "heteroaromatic". The term "heteroaralkyl" refers to an alkyl group substituted with a heteroaryl group. The term "heteroarylalkoxy" refers to an alkoxy group substituted with a heteroaryl group.

Heteroaryl groups include, without limitation, furanyl, imidazolyl, isoxazolyl, oxadiazolyl, oxazolyl, pyrrolyl, pyridyl, pyrimidyl, pyridazinyl, thiazolyl, tetrazolyl, triazolyl, thienyl, benzimidazolyl, benzothienyl, benzofuranyl, indolyl, quinolinyl, benzothiazolyl, benzoxazolyl, benzimidazolyl, isoquinolinyl, isoindolyl, acridinyl, benzoisoxazolyl, tetrahydroquinolinyl, tetrahydroisoquinolinyl, and pyrido[3,4-d]pyrimidinyl.

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylene-dioxy; 1,2-ethylenedioxy; phenyl (Ph) optionally substituted with R°; —O(Ph) optionally substituted with R°; —NO$_2$; —CN; —N(R°)$_2$; —NR°C(O)R°; —NR°C(O)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(O)N(R°)$_2$; —OC(O)N(R°)$_2$; —S(O)$_2$R°; —SO$_2$N(R°)$_2$; —S(O)R°; —NR°SO$_2$N(R°)$_2$; —NR°SO$_2$R°; —C(=S)N(R°)$_2$; —C(=NH)—N(R°)$_2$; or —(CH$_2$)$_{1-2}$NHC(O)R° wherein each independent occurrence of R° is selected from hydrogen, optionally substituted C$_{1-6}$ aliphatic, an unsubstituted 5–6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$aliphatic), or haloC$_{1-4}$aliphatic, wherein each of the foregoing C$_{1-4}$aliphatic groups of R° is unsubstituted.

An aliphatic or heteroaliphatic group including a non-aromatic heterocyclic ring may contain one or more substituents. Suitable substituents on the saturated carbon of an aliphatic or heteroaliphatic group including a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —(CH$_2$)$_{1-2}$(Ph), optionally substituted —CH=CH(Ph), or an unsubstituted 5–6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3–8-membered cycloalkyl, heterocyclyl, aryl, or heteroaryl ring having 0–3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched hydrocarbon chain that may be fully saturated or have one or more units of unsaturation and has two points of attachment to the rest of the molecule.

As detailed above, in some embodiments, two independent occurrences of R° (or R$^+$, or any other variable similarly defined herein), are taken together with the atom(s) to which each variable is bound to form a 3–8-membered cycloalkyl, heterocyclyl, aryl, or heteroaryl ring having 0–3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

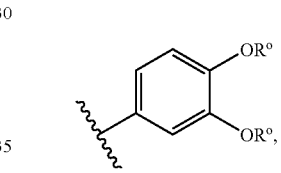

these two occurrences of R° are taken together with the oxygen atoms to which they are bound to form a fused 6-membered oxygen-containing ring:

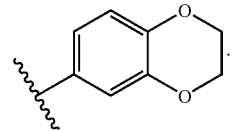

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

In certain embodiments of the invention, W is oxygen. In other embodiments, W is sulfur. In some embodiments of the invention, ring A is phenyl substituted with 1–4 groups independently selected from halo, —R$^1$, —OR$^1$, —SR$^1$, —NO$_2$, —CN, —N(R$^1$)$_2$, —NR$^1$C(O)R$^1$, —NR$^1$C(O)N(R$^1$)$_2$, —NR$^1$CO$_2$R$^1$, —NR$^1$NR$^1$C(O)R$^1$, —NR$^1$NR$^1$C(O)N(R$^1$)$_2$, —NR$^1$NR$^1$CO$_2$R$^1$, —C(O)C(O)R$^1$, —C(O)CH$_2$C(O)R$^1$, —CO$_2$R$^1$, —C(O)R$^1$, —C(O)N(R$^1$)$_2$, —OC(O)N(R$^1$)$_2$, —S(O)$_2$R$^1$, —SO$_2$N(R$^1$)$_2$, —S(O)R$^1$, —NR$^1$SO$_2$R$^1$, —NR$^1$SO$_2$N(R$^1$)$_2$, —C(=S)N(R$^1$)$_2$, or —C(=NH)—N(R$^1$)$_2$, wherein two independent occurrences of R$^1$, on the same substituent or different substituents, optionally taken together with the atom or atoms to which each R$^1$ group is bound, form a 5–7-membered cycloalkyl, heterocyclyl, aryl, or heteroaryl ring having 0–2 heteroatoms independently selected from N, O or S.

In certain embodiments of the invention, W is oxygen or sulfur and ring A is phenyl substituted with 1–4 groups independently selected from halo, —R$^1$, —OR$^1$, —SR$^1$, —NO$_2$, —CN, —N(R$^1$)$_2$, —NR$^1$C(O)R$^1$, —CO$_2$R$^1$, —C(O)R$^1$, —C(O)N(R$^1$)$_2$, —S(O)$_2$R$^1$, —SO$_2$N(R$^1$)$_2$, —NR$^1$SO$_2$R$^1$, or —C(=S)N(R$^1$)$_2$, wherein two independent occurrences of R$^1$, on the same substituent or different substituents, optionally taken together with the atom or atoms to which each R$^1$ group is bound, form a 5–7-membered heterocyclyl, aryl, or heteroaryl ring having 0–2 heteroatoms independently selected from N, O or S.

In other embodiments, W is oxygen or sulfur and ring A is a 5–6 membered heterocyclyl or heteraryl ring having 1–2 heteroatoms independently selected from N, O or S, wherein ring A is optionally substituted with 1–4 groups independently selected from halo, —R$^1$, —OR$^1$, —SR$^1$, —NO$_2$, —CN, —N(R$^1$)$_2$, —NR$^1$C(O)R$^1$, —CO$_2$R$^1$, —C(O)R$^1$, —C(O)N(R$^1$)$_2$, —S(O)$_2$R$^1$, —SO$_2$N(R$^1$)$_2$, —NR$^1$SO$_2$R$^1$, or —C(=S)N(R$^1$)$_2$, wherein two independent occurrences of R$^1$, on the same substituent or different substituents, optionally taken together with the atom or atoms to which each R$^1$ group is bound, form a 5–7-membered cycloalkyl, heterocyclyl, aryl, or heteroaryl ring having 0–2 heteroatoms independently selected from N, O or S.

In certain embodiments, W is oxygen or sulfur and ring A is naphthyl, benzodioxolyl, dihydrobenzodioxinyl, benzothiazolyl, benzoimidazolyl, or dihydrobenzo[b][1,4]dioxepinyl, wherein each member of ring A is optionally substituted with halo, —R$^2$, —OR$^2$, —SR$^2$, —NO$_2$, —CN, —N(R$^2$)$_2$, —NR$^2$C(O)R$^2$, —CO$_2$R$^2$, —C(O)R$^2$, —C(O)N(R$^2$)$_2$, —S(O)$_2$R$^2$, —SO$_2$N(R$^2$)$_2$, —NR$^2$SO$_2$R$^2$, or —C(=S)N(R$^2$)$_2$.

In some embodiments, W is oxygen or sulfur and ring A is pyridinonyl, tetrahydroquinolinyl, pyridyl, or thiazolyl, wherein each member of ring A is optionally substituted with halo, —R$^2$, —OR$^2$, —SR$^2$, —NO$_2$, —CN, —N(R$^2$)$_2$, —NR$^2$C(O)R$^2$, —CO$_2$R$^2$, —C(O)R$^2$, —C(O)N(R$^2$)$_2$, —S(O)$_2$R$^2$, —SO$_2$N(R$^2$)$_2$, —NR$^2$SO$_2$R$^2$, or —C(=S)N(R$^2$)$_2$.

Representative examples of compounds of the present invention are shown below in Table 1.

TABLE 1

Examples of Compounds of Formula I:

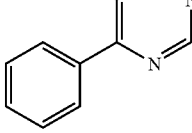

I-1

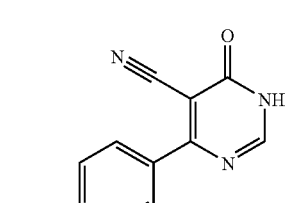

I-2

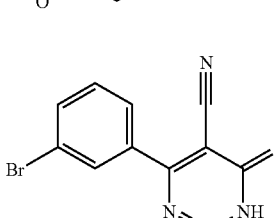

I-3

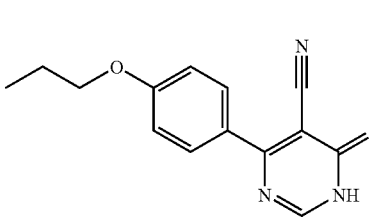

I-4

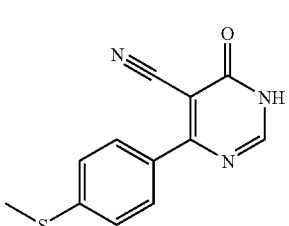

I-5

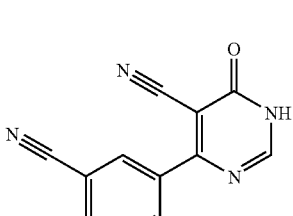

I-6

TABLE 1-continued
Examples of Compounds of Formula I:
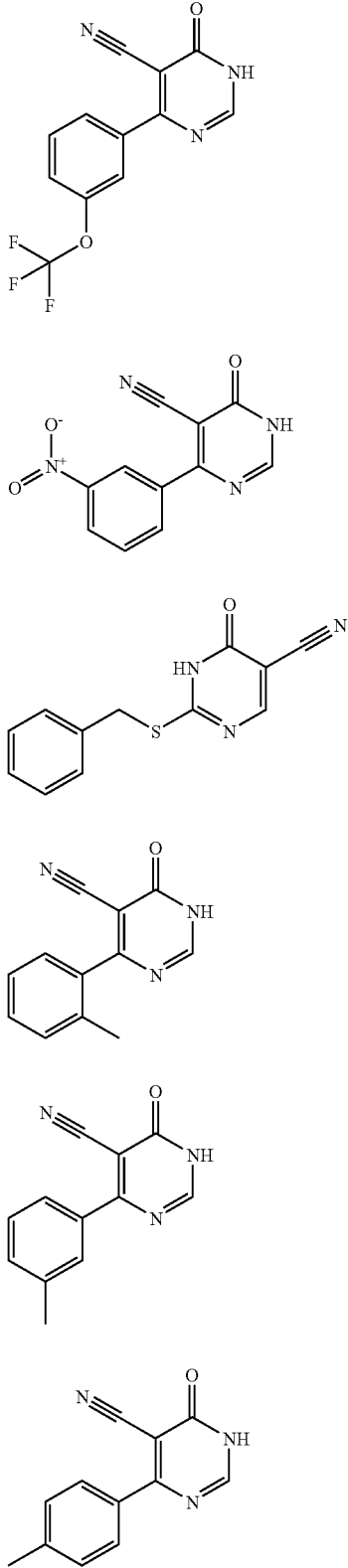
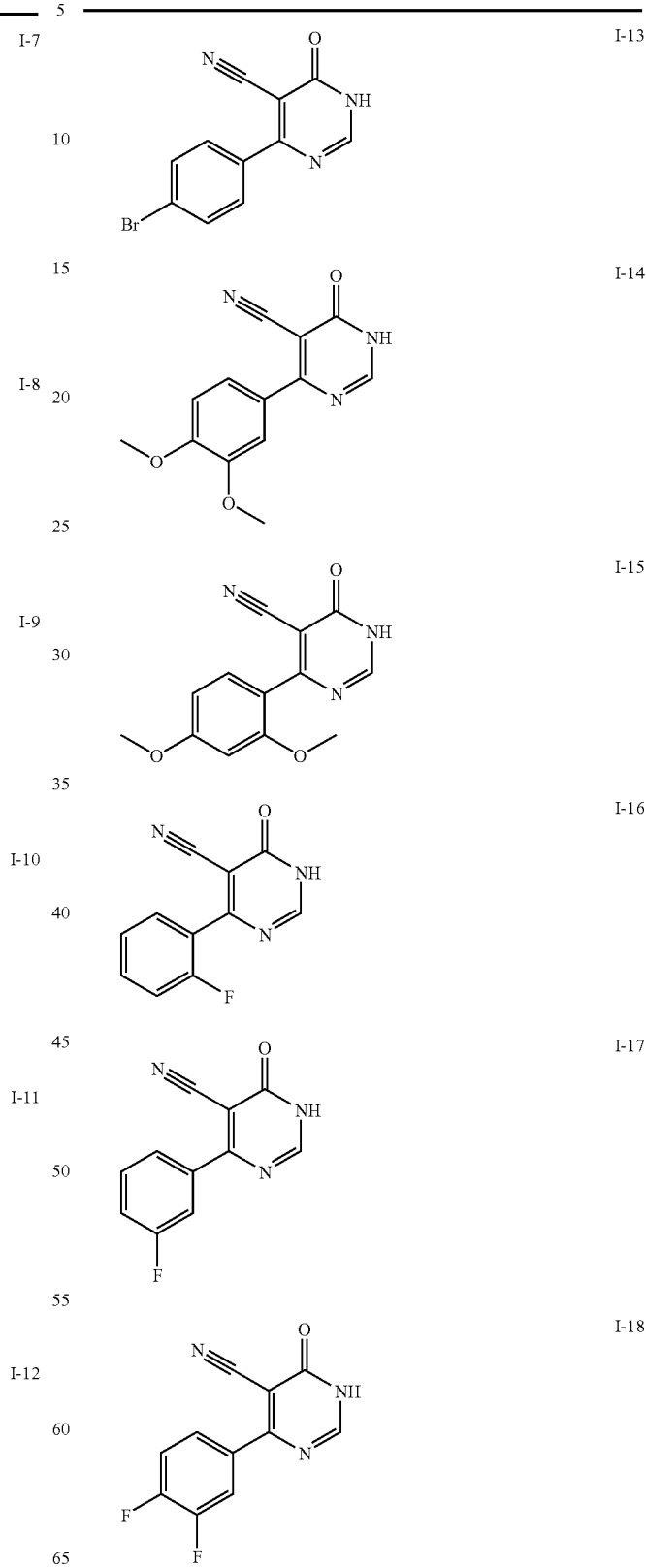

TABLE 1-continued
Examples of Compounds of Formula I:
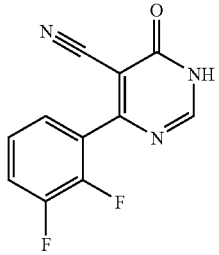
I-19
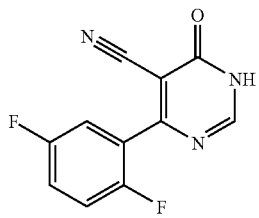
I-20
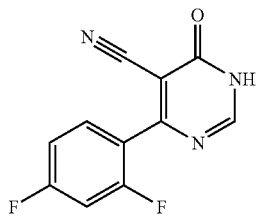
I-21
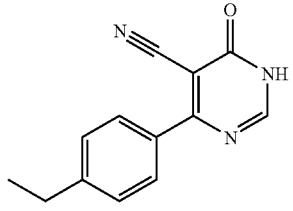
I-22
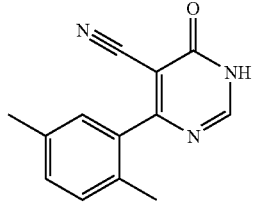
I-23
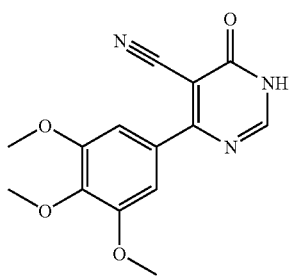
I-24
TABLE 1-continued
Examples of Compounds of Formula I:
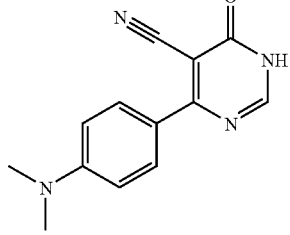
I-25
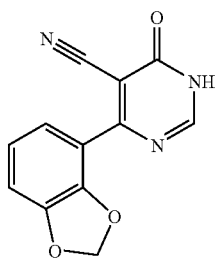
I-26
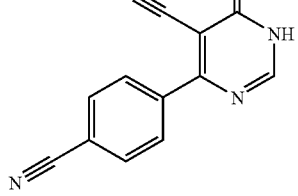
I-27
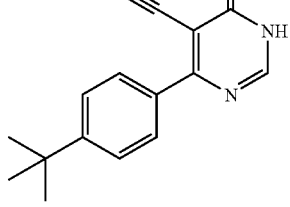
I-28
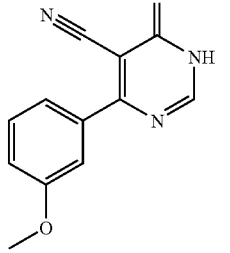
I-29
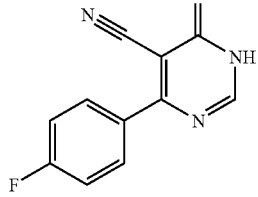
I-30

TABLE 1-continued
Examples of Compounds of Formula I:
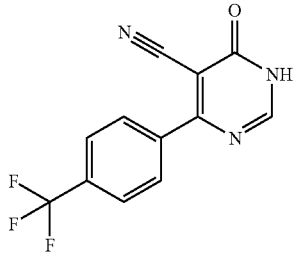
I-31
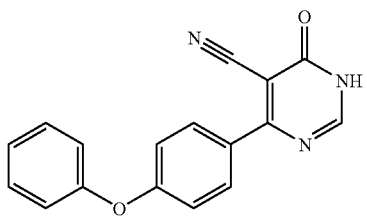
I-32
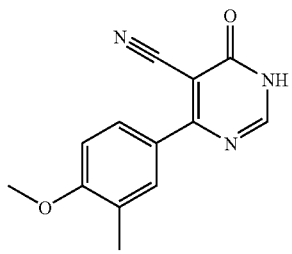
I-33
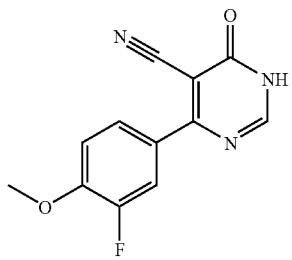
I-34
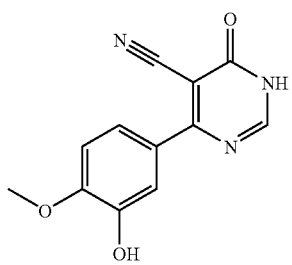
I-35
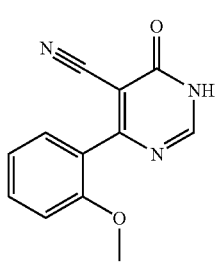
I-36
TABLE 1-continued
Examples of Compounds of Formula I:
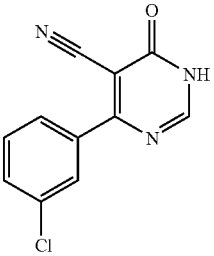
I-37
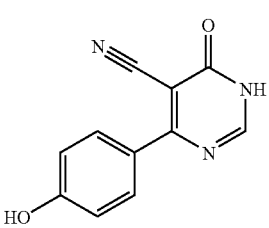
I-38
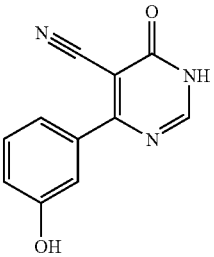
I-39
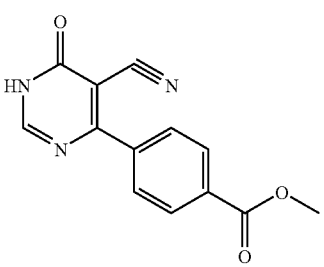
I-40
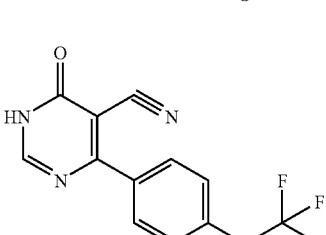
I-41
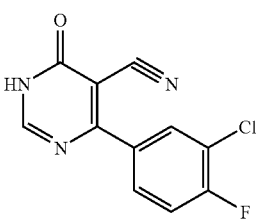
I-42

TABLE 1-continued
Examples of Compounds of Formula I:
I-43
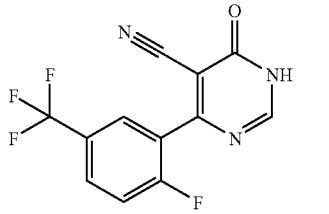
I-44
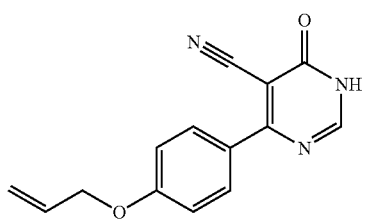
I-45
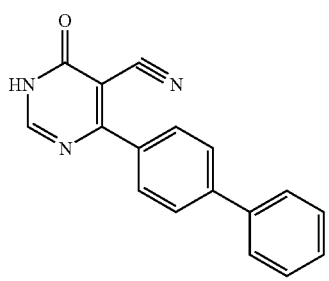
I-46
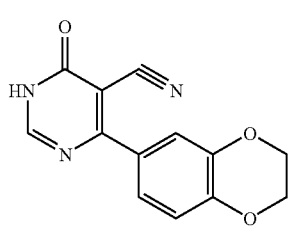
I-47
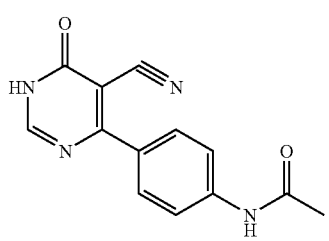
I-48
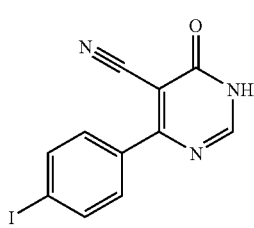
TABLE 1-continued
Examples of Compounds of Formula I:
I-49
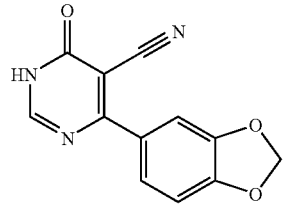
I-50
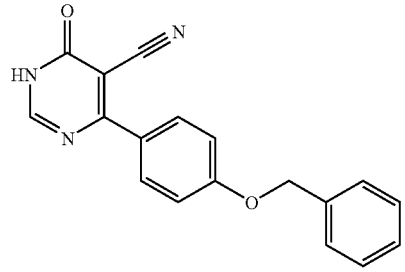
I-51
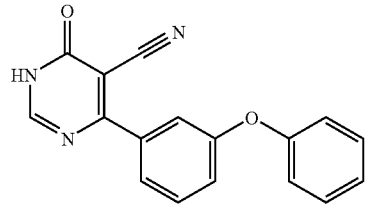
I-52
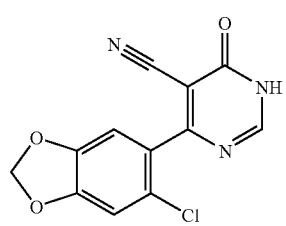
I-53
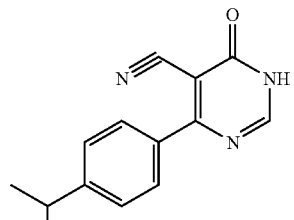
I-54
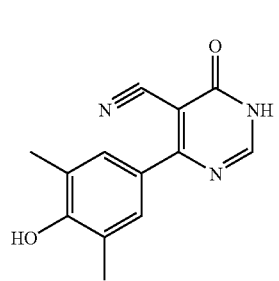

TABLE 1-continued
Examples of Compounds of Formula I:
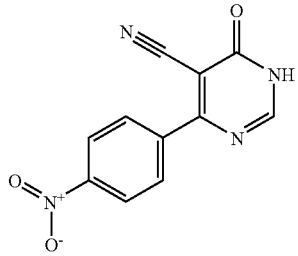
I-55
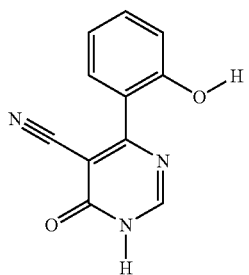
I-56
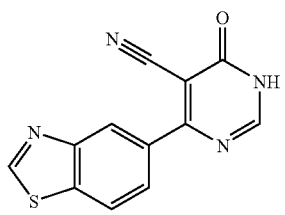
I-57
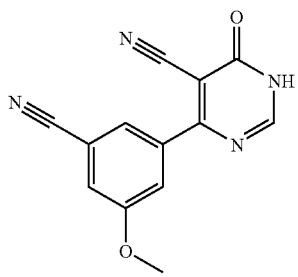
I-58
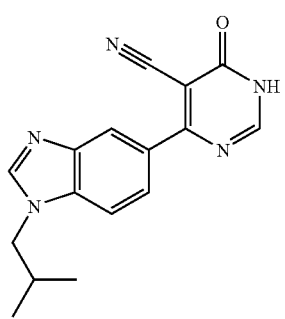
I-59
TABLE 1-continued
Examples of Compounds of Formula I:
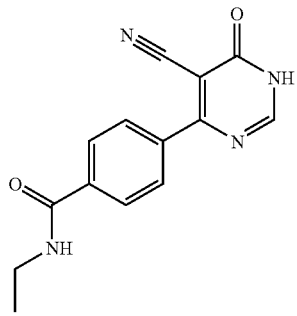
I-60
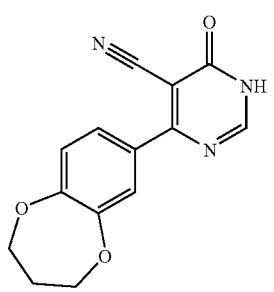
I-61
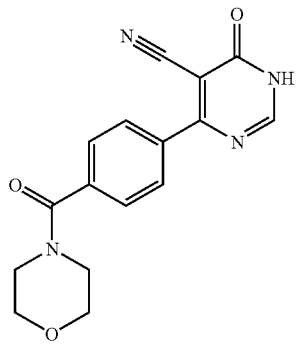
I-62
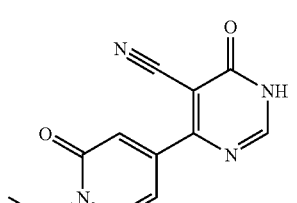
I-63
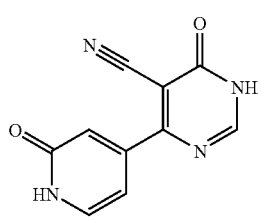
I-64

TABLE 1-continued

Examples of Compounds of Formula I:

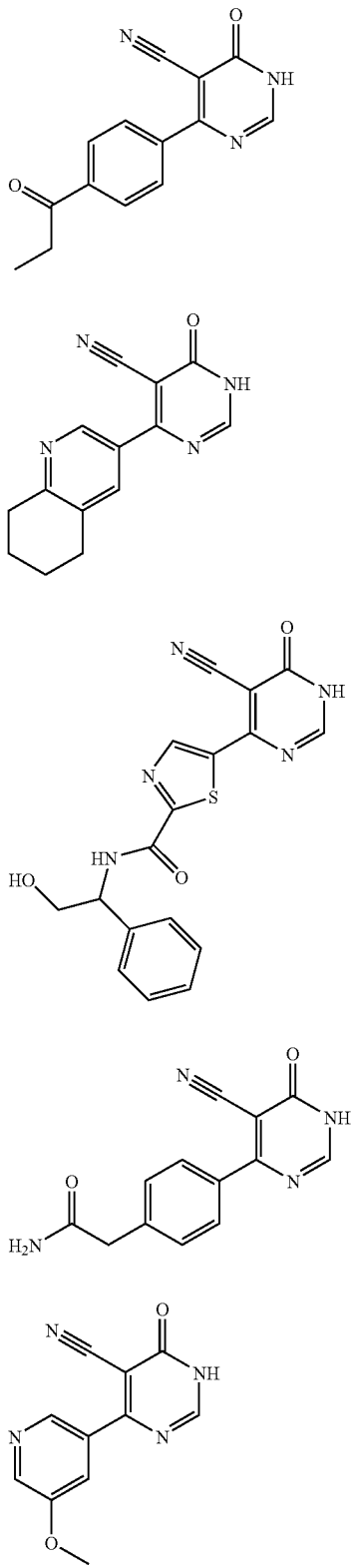

I-65

I-66

I-67

I-68

I-69

4. General Synthetic Methodology:

The compounds of this invention may be prepared in general by methods known to those skilled in the art for analogous compounds, as illustrated by the general schemes below.

Scheme I

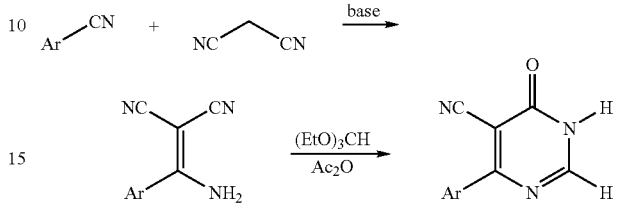

Scheme I above shows a synthetic route (as described by Z. Naturforsch. B, 1979, 34B (11), 1580–1586) for preparing certain exemplary compounds of the present invention when W is oxygen and ring A is Ar wherein Ar denotes an optionally substituted aromatic moiety.

Scheme II

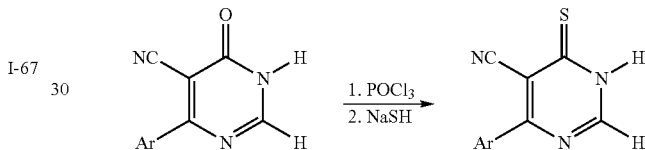

Scheme II above shows a synthetic route (as described in Chem. Ber., 1967, 100 (11), 3664–3670) for preparing compounds of formula I wherein W is sulfur from compounds of formula I when W is oxygen, wherein ring A is Ar wherein Ar denotes an optionally substituted aromatic moiety.

Although certain exemplary embodiments are depicted and described above and herein, it will be appreciated that compounds of the invention can be prepared according to the methods described generally above using appropriate starting materials and/or by methods generally available to one of skill in the art. Appropriate functional group manipulations such as protection and deprotection may be required in preparing compounds of the present invention using the general schemes above. Protection and deprotection techniques are described, for example, in "Protective Groups in Organic Synthesis", Third Ed. Greene, T. W. and Wuts, P. G., Eds., John Wiley & Sons, New York: 1999, the content of which is hereby incorporated by reference.

5. Uses, Formulation and Administration

Pharmaceutically Acceptable Compositions

As discussed above, the present invention provides compounds that are inhibitors of GSK-3, and thus the present compounds are useful for the treatment of diseases, disorders, and conditions including, but not limited to, autoimmune diseases, inflammatory diseases, metabolic, neurological and neurodegenerative diseases, cardiovascular diseases, allergy, asthma, diabetes, Alzheimer's disease, Huntington's Disease, Parkinson's Disease, AIDS-associated dementia, amyotrophic lateral sclerosis (AML, Lou Gehrig's Disease), multiple sclerosis (MS), schizophrenia, cardiomyocyte hypertrophy, reperfusion/ischemia, and baldness. Accordingly, in another aspect of the present invention, pharmaceutically acceptable compositions are provided, wherein these compositions comprise any of the compounds as described herein, and a pharmaceutically acceptable carrier, adjuvant or vehicle. In certain embodiments, these compositions optionally further comprise one or more additional therapeutic agents.

It will also be appreciated that compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need thereof is capable of providing, directly or indirectly, a compound as otherwise described herein, or an inhibitorily active metabolite or residue thereof.

As used herein, the term "pharmaceutically acceptable" means within the scope of sound medical judgement, suitable for use in contact with the tissues of patients (e.g., humans and lower animals) without undue toxicity, irritation, allergic response and the like, and commensurate with a reasonable benefit/risk ratio. As used herein, the term "inhibitorily active metabolite or residue" means that a metabolite or residue of a compound of the present invention is also an inhibitor of GSK-3. Such inhibitorily active metabolites or residues are expressly included within the scope of this invention.

Pharmaceutically acceptable salts are well known in the art. For example, S. M. Berge, et al. describe pharmaceutically acceptable salts in detail in *J. Pharmaceutical Sciences*, 1977, 66, 1–19, incorporated herein by reference. Pharmaceutically acceptable salts of the compounds of this invention include those derived from suitable inorganic and organic acids and bases. Examples of pharmaceutically acceptable, nontoxic acid addition salts are, but not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include, but are not limited to, alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, aryl sulfonate, and the like.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers; alumina; aluminum stearate; lecithin; serum proteins, such as human serum albumin; buffer substances such as phosphates; glycine; sorbic acid or potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and other non-toxic compatible lubricants such as sodium lauryl sulfate and magnesium stearate; as well as coloring agents, releasing agents, coating agents, and sweetening, flavoring and perfuming agents. Preservatives and antioxidants can also be present in the composition, according to the judgment of the formulator.

Uses of Compounds and Pharmaceutically Acceptable Compositions

In yet another aspect, a method for treating or lessening the severity of GSK-3-mediated diseases, disorders and/or conditions is provided comprising administering an effective amount of a compound or a pharmaceutically acceptable composition of the present invention to a patient in need thereof. In certain embodiments of the present invention, an "effective amount" of the compound or pharmaceutical composition is an amount effective for treating or lessening GSK-3-mediated diseases, disorders and/or conditions. The compounds and compositions, according to the method of the present invention, may be administered using any amount and any route of administration effective for treating or lessening the severity of GSK-3-mediated diseases, disorders and/or conditions. The exact amount required will vary from patient to patient, depending on the species, age, and general condition of the patient, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to patients (e.g., humans and other animals) orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of patient body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- and diglycerides. In addition, fatty acids such as oleic acid can be used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol and a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that releases the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that can release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds and compositions of the invention are useful as inhibitors of GSK-3, and thus, without wishing to be bound by any particular theory, the compounds and compositions are particularly useful for treating or lessening the severity of a disease, condition, or disorder where activation of GSK-3 is implicated in the disease, condition, or disorder. When activation of GSK-3 is implicated in a particular disease, condition, or disorder, the disease, condition, or disorder may also be referred to as "GSK-3-mediated disease" or disease symptom.

The activity of a compound utilized in this invention as an inhibitor of GSK-3, may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

The term "measurably inhibit", as used herein, means a measurable change in GSK-3 activity between a sample comprising said composition and glycogen synthase kinase-3 and an equivalent sample comprising glycogen synthase kinase-3 kinase in the absence of said composition. In some embodiments, compounds of the present invention inhibit the kinase activity at least 50%. In other embodiments, compounds of the present invention inhibit the kinase activity at least 60% to 70%. In certain embodiments, compounds of the present invention inhibit the kinase activity at least 80% to 90%. In some embodiments of the invention, compounds of the present invention inhibit the kinase activity at least 95%. Any method known in the art may be used to measure the change in the kinase activity.

The term "GSK-3-mediated disease, disorder, and/or condition" as used herein, means any disease or other deleterious condition or disorder in which GSK-3 is known to play a role. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

In other embodiments, the invention relates to a method of enhancing glycogen synthesis and/or lowering blood levels of glucose in a patient in need thereof, comprising administering to said patient a therapeutically effective amount of a compound of formula I or a composition thereof. This method is especially useful for diabetic patients.

In yet another embodiment, the invention relates to a method of inhibiting the production of hyperphosphorylated Tau protein in a patient in need thereof, comprising administering to said patient a therapeutically effective amount of a compound of formula I or a composition thereof. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a compound of formula I or a composition thereof. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, disorder or condition, are known as "appropriate for the disease, disorder, or condition being treated".

Other examples of agents that the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and agents for treating diabetes such as insulin, in injectable or inhalation form, glitazones, and sulfonyl ureas.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to a method of inhibiting GSK-3 activity in a biological sample or a patient in need thereof, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3 activity in a biological sample is useful for a variety of purposes that are known to one of skill in the art. Examples of such purposes include, but are not limited to, blood transfusion, organ-transplantation, biological specimen storage, and biological assays.

EXAMPLE 1

GSK-3 Inhibition Assay

Compounds are screened for their ability to inhibit GSK-3β (AA 1–420) activity using a standard coupled enzyme system (Fox et al. (1998) *Protein Sci.* 7, 2249). Reactions are carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay are 20 µM ATP (Sigma Chemicals, St Louis, Mo.) and 300 µM peptide (American Peptide, Sunnyvale, Calif.). Reactions are carried out at 30° C. and 20 nM GSK-3β. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and the test compound of interest. The assay stock buffer solution (175 µl) is incubated in a 96 well plate with 5 µl of the test compound of interest at final concentrations spanning 0.002 µM to 30 µM at 30° C. for 10 minutes. Typically, a 12 point titration is conducted by preparing serial dilutions (from 10 mM compound stocks) with DMSO of the test compounds in daughter plates. The reaction is initiated by the addition of 20 µl of ATP (final concentration 20 µM). Rates of reaction are obtained using a Molecular Devices Spectramax plate reader (Sunnyvale, Calif.) over 10 minutes at 30° C. The $K_i$ values are determined from the rate data as a function of inhibitor concentration.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound of formula I:

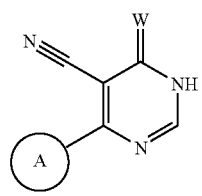

or a pharmaceutically acceptable salt thereof, wherein:

W is oxygen or sulfur;

ring A is a 5–6 membered aryl, heterocyclyl or heteroaryl ring having 0–4 heteroatoms independently selected from nitrogen, oxygen, or sulfur;

wherein ring A is optionally substituted with 1–4 groups independently selected from halo; aliphatic, aryl, heteroaryl or heterocyclyl, wherein said aliphatic, aryl, heteroaryl or heterocyclyl is optionally substituted with halo, $-R^2$, $-OR^2$, $-SR^2$, $-NO_2$, $-CN$, $-N(R^2)_2$, $-NR^2C(O)R^2$, $NR^2C(O)N(R^2)_2$, $-NR^2CO_2R^2$, $-NR^2NR^2C(O)R^2$, $-NR^2NR^2C(O)N(R^2)_2$, $-NR^2NR^2CO_2R^2$, $-C(O)C(O)R_2$, $-C(O)CH_2C(O)R^2$, $-CO^2R^2$, $-C(O)R^2$, $-C(O)N(R^2)^2$, $-OC(O)N(R^2)_2$, $-S(O)_2R^2$, $-SO_2N(R^2)_2$, $-S(O)R^2$, $-NR^2SO_2R^2$, $-NR^2SO_2N(R^2)_2$, $-C(=S)N(R^2)_2$, $-C(=NH)-N(R^2)_2$, $=O$, $=S$, $=NNHR^2$, $=NN(R^2)_2$, $=NNHC(O)R^2$, $=NNHCO_2(R^2)$, $=NNHSO^2(R^2)$, or $=NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur;

$-SR^1$, $-NO_2$, $-CN$, $-N(R^1)_2$, $-NR^1C(O)R^1$, $-NR^1C(O)N(R^1)_2$, $-NR^1CO_2R^1$, $-NR^1NR^1C(O)R^1$, $-NR^1NR^1C(O)N(R^1)_2$, $-NR^1NR^1CO^2R^1$, $-C(O)C(O)R^1$, $-C(O)CH^2C(O)R^1$, $-CO^2R^1$, $-C(O)R^1$, $-C(O)N(R^1)_2$, $-OC(O)N(R^1)_2$, $-S(O)_2R^1$, $-SO_2N(R^1)_2$, $-S(O)R^1$, $-NR^1SO_2R^1$, $-NR^1SO_2N(R^1)_2$, $-C(=S)N(R^1)_2$, $-C(=NH)-N(R^1)_2$, $=O$, $=S$, $=NNHR^1$, $=NN(R^1)_2$, $=NNHC(O)R^1$, $=NNHCO_2(R^1)$, $=NNHSO_2(R^1)$, or $=NR^1$, wherein two independent occurrences of $R^1$, on the same substituent or different substituents, optionally taken together with the atom or atoms to which each $R^1$ group is bound, form a 3–8 membered cycloalkyl, heterocyclyl, aryl, or heteroaryl ring having 0–3 heteroatoms independently selected from nitrogen, oxygen, or sulfur;

each $R^1$ is independently selected from hydrogen, aliphatic, aryl, heteroaryl or heterocyclyl, wherein each member of $R^1$ except hydrogen is optionally substituted with halo, $-R^2$, $-OR^2$, $-SR^2$, $-NO_2$, $-CN$, $-N(R^2)_2$, $-NR^2C(O)R^2$, $-NR^2C(O)N(R^2)_2$, $-NR^2CO^2R^2$, $-NR^2NR^2C(O)R^2$, $-NR^2NR^2C(O)N(R^2)_2$, $-NR^2NR^2CO_2R^2$, $-C(O)C(O)R^2$, $-C(O)CH_2C(O)R^2$, $-CO_2R^2$, $-C(O)R^2$, $-C(O)N(R^2)_2$, $-OC(O)N(R^2)_2$, $-S(O)_2R^2$, $-SO_2N(R^2)_2$, $-S(O)R^2$, $-NR^2SO_2R^2$, $-NR^2SO_2N(R^2)_2$, $-C(=S)N(R^2)_2$, $-C(=NH)-N(R^2)_2$, $=O$, $=S$, $=NNHR^2$, $=NN(R^2)_2$, $=NNHC(O)R^2$, $=NNHCO_2(R^2)$, $=NNHSO^2(R^2)$, or $=NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur;

each $R^2$ is independently selected from hydrogen, aliphatic, aryl, heteroaryl or heterocyclyl, wherein each member of $R^2$ except hydrogen is optionally substituted with halo, $-R^3$, $-OR^3$, $-SR^3$, $-NO^2$, $-CN$, $-N(R^3)_2$, $-NR^3C(O)R^3$, $-NR^3C(O)N(R^3)_2$, $-NR^3CO_2R^3$, $^3NR^3C(O)R^3$, $-NR^3NR^3C(O)N(R^3)_2$, $-NR^3NR^3CO_2R^3$, $-C(O)C(O)R^3$, $-C(O)CH^2C(O)R^3$, $-CO^2R^3$, $-C(O)R^3$, $-C(O)N(R^3)_2$, $-OC(O)N(R^3)_2$, $-S(O)_2R^3$, $-SO_2N(R^3)_2$, $-S(O)R^3$, $-NR^3SO_2R^3$, $-NR^3SO^2N(R^3)_2$, $-C(=S)N(R^3)_2$, $-C(=NH)-N(R^3)_2$, $=O$, $=S$, $=NNHR^3$, $=NN(R^3)_2$, $=NNHC(O)R^3$, $=NNHCO_2(R^3)$, $=NNHSO_2(R^3)$, or $=NR^3$; and each $R^3$ is independently hydrogen or unsubstituted aliphatic;

provided that when ring A is phenyl, it must be substituted.

2. The compound of claim 1, wherein W is oxygen.

3. The compound of claim 1, wherein W is sulfur.

4. The compound of claim 2 or 3, wherein ring A is phenyl substituted with 1–4 groups independently selected from halo; aliphatic, aryl, heteroaryl or heterocyclyl, wherein said aliphatic, aryl, heteroaryl or heterocyclyl is optionally substituted with halo, $-R^2$, $-OR^2$, $-SR^2$, $-NO^2$, $-CN$, $-N(R^2)_2$, $-NR^2C(O)R^2$, $-NR^2C(O)N(R^2)_2$, $-NR^2CO_2R^2$, $-NR^2NR^2C(O)R^2$, $-NR^2NR^2C(O)N(R^2)_2$, $-NR^2NR^2CO_2R^2$, $-C(O)C(O)R^2$, $-C(O)CH^2C(O)R^2$, $-CO^2R^2$, $-C(O)R^2$, $-C(O)N(R^2)_2$, $-OC(O)N(R^2)_2$, $-S(O)_2R^2$, $-SO^2N(R^2)_2$, $-S(O)R^2$, $-NR^2SO^2R^2$, $-NR_2SO_2N(R^2)_2$, $-C(=S)N(R^2)_2$, $-C(=NH)-N(R^2)_2$, $=O$, $=S$, $=NNHR^2$, $=NN(R^2)_2$, $=NNHC(O)R^2$, $=NNHCO^2(R^2)$, $=NNHSO^2(R^2)$, or $=NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur; $-SR^1$, $-NO_2$, $-CN$, $-N(R^1)_2$, $-NR^1C(O)R^1$, $-NR^1C(O)N(R^1)_2$, $-NR^1CO_2R^1$, $-NR^1NR^1C(O)R^1$, $-NR^1NR^1C(O)N(R^1)_2$, $-NR^1NR^1CO^2R^1$, $-C(O)C(O)R^1$, $-C(O)CH^2C(C)R^1$, $-CO^2R^1$, $-C(O)R^1$, $-C(O)N(R^1)_2$, $-OC(O)N(R^1)_2$, $-S(O)_2R^1$, $-SO^2N(R^1)_2$, $-S(O)R^1$, $-NR^1SO_2R^1$, $-NR^1SO_2N(R^1)_2$, $-C(=S)N(R^1)_2$, or $-C(=NH)-N(R^1)^2$, wherein two independent occurrences of $R^1$, on the same substituent or different substituents, optionally taken together with the atom or atoms to which each $R^1$ group is bound, form a 5–7-membered cycloalkyl, heterocyclyl, aryl, or heteroaryl ring having 0–2 heteroatoms independently selected from N, O or S.

5. The compound of claim 4, wherein ring A is phenyl substituted with 1–4 groups independently selected from halo; aliphatic, aryl, heteroaryl or heterocyclyl, wherein said aliphatic, aryl, heteroaryl or heterocyclyl is optionally substituted with halo, $-R^2$, $-OR^2$, $-SR^2$, $-NO_2$, $-CN$, $-N(R^2)_2$, $-NR^2C(O)R^2$, $-NR^2C(O)N(R^2)_2$, $-NR^2CO^2R^2$, $-NR^2NR^2C(O)R^2$, $-NR^2NR^2C(O)N(R^2)_2$, $-NR^2NR^2CO_2R^2$, $-C(O)C(O)R^2$, $-C(O)CH^2C(O)R^2$, $-CO^2R^2$, $-C(O)R^2$, $-C(O)N(R^2)_2$, $-OC(O)N(R^2)_2$, $-S(O)_2R^2$, $-SO_2N(R^2)_2$, $-S(O)R^2$, $-NR^2SO_2R^2$, $-NR^2SO_2N(R^2)_2$, $-C(=S)N(R^2)_2$, $-C(=NH)-N(R^2)_2$, $=O$, $=S$, $=NNHR^2$, $=NN(R^2)^2$, $=NNHC(O)R^2$, $=NNHCO^2(R^2)$, $=NNHSO^2(R^2)$, or $=NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur; $-SR^1$, $-NO_2$, $-CN$, $-N(R^1)_2$, $-NR^1C(O)R^1$, $-CO_2R^1$, $-C(O)R^1$, $-C(O)N(R^1)_2$, $-S(O)_2R^1$, $-SO^2N(R^1)_2$, $-NR^1SO_2R^1$, or $-C(=S)N(R^1)_2$, wherein two independent occurrences of $R^1$, on the same substituent or different substituents, optionally taken together with the atom or atoms to which each $R^1$ group is bound, form a 5–7-membered heterocyclyl, aryl, or heteroaryl ring having 0–2 heteroatoms independently selected from N, O or S.

6. A compound of formula I:

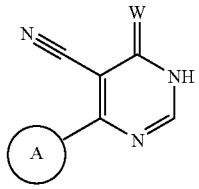

I or a pharmaceutically acceptable salt thereof, wherein:
W is oxygen or sulfur;
ring A is naphthyl, benzodioxolyl, dihydrobenzodioxinyl, benzothiazolyl, benzoimidazolyl, or dihydrobenzo, dioxepinyl, wherein each member of ring A is optionally substituted with halo, $R^2$, —$OR^2$, —$SR^2$, —$NO_2$, —CN, —$N(R^2)_2$, —$NR^2C(O)R^2$, —$CO_2R^2$, —$C(O)R^2$, —$C(O)N(R^2)_2$, —$S(O)_2R^2$, —$SO_2N(R^2)_2$, —$NR^2SO_2R^2R^2$, or —$C(=S)N(R^2)_2$;
each $R^2$ is independently selected from hydrogen, aliphatic, aryl, heteroaryl or heterocyclyl, wherein each member of $R^2$ except hydrogen is optionally substituted with halo, —$R^3$, —$OR^3$, —$SR^3$, —$NO^2$, —CN, —$N(R^3)_2$, —$NR^3C(O)R^3$, —$NR^3C(O)N(R^3)_2$, —$NR^3CO_2R^3$, —$NR^3NR^3C(O)R^3$, —$NR^3NR^3C(O)N(R^3)_2$, —$NR^3NR^3CO_2R^3$, —$C(O)C(O)R^3$, —$C(O)CH_2C(O)R^3$, —$CO_2R^3$, —$C(O)R^3$, —$C(O)N(R^3)_2$, —$OC(O)N(R^3)_2$, —$S(O)_2R^3$, —$SO_2N(R^3)_2$, —$S(O)R^3$, —$NR^3SO^2R^3$, —$NR^3SO_2N(R^3)_2$, —$C(=S)N(R^3)_2$, —$C(=NH)$—$N(R^3)_2$, =O, =S, =NNHR$^3$, =NN(R$^3$)$_2$, =NNHC(O)R$^3$, =NNHCO$^2$(R$^3$), =NNHSO$_2$(R$^3$), or =NR$^3$; and
each $R^3$ is independently hydrogen or trisubstituted aliphatic.

7. A compound selected from:

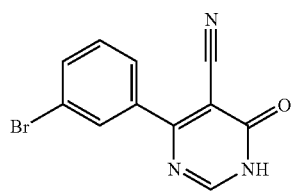
I-3

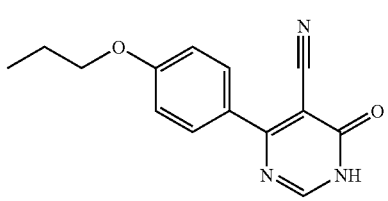
I-4

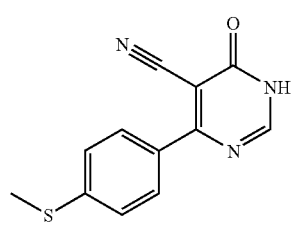
I-5

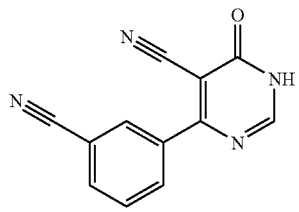
I-6

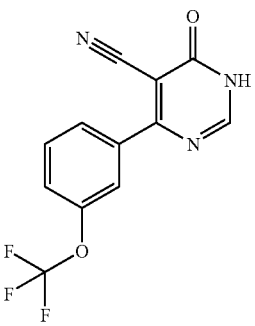
I-7

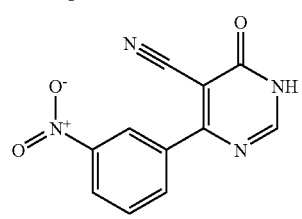
I-8

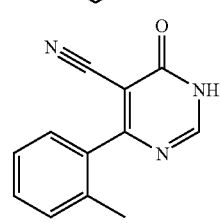
I-10

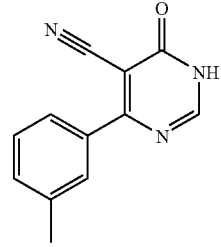
I-11

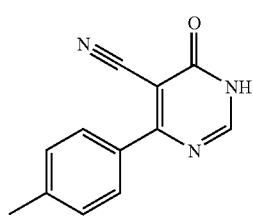
I-12

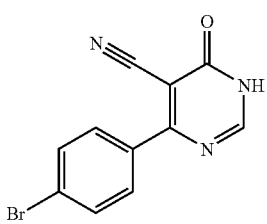
I-13

-continued
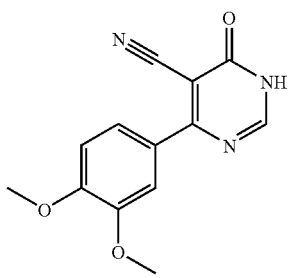
I-14
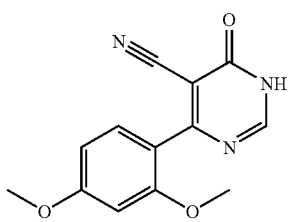
I-15
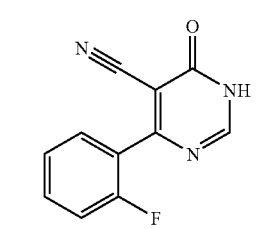
I-16
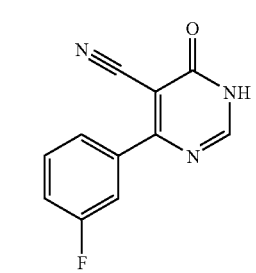
I-17
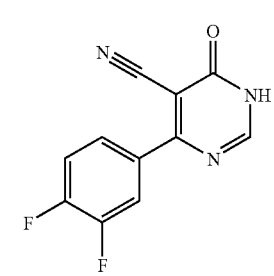
I-18
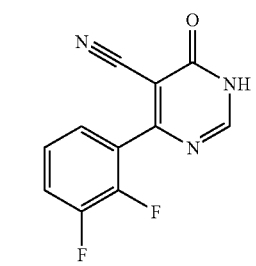
I-19
-continued
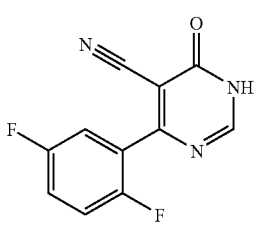
I-20
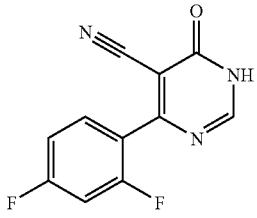
I-21
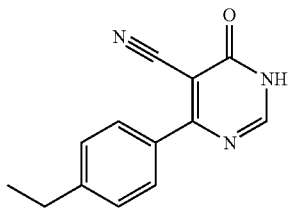
I-22
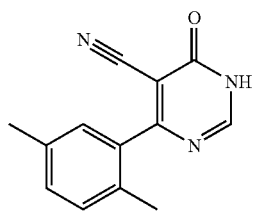
I-23
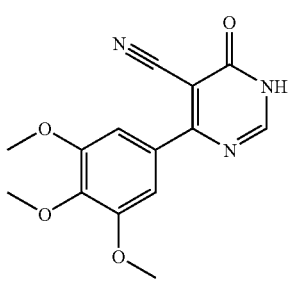
I-24
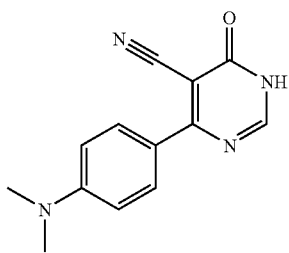
I-25

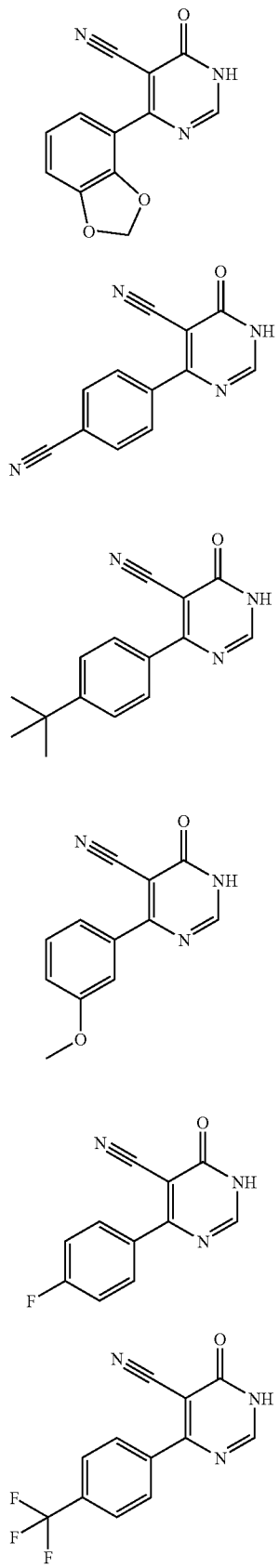

-continued
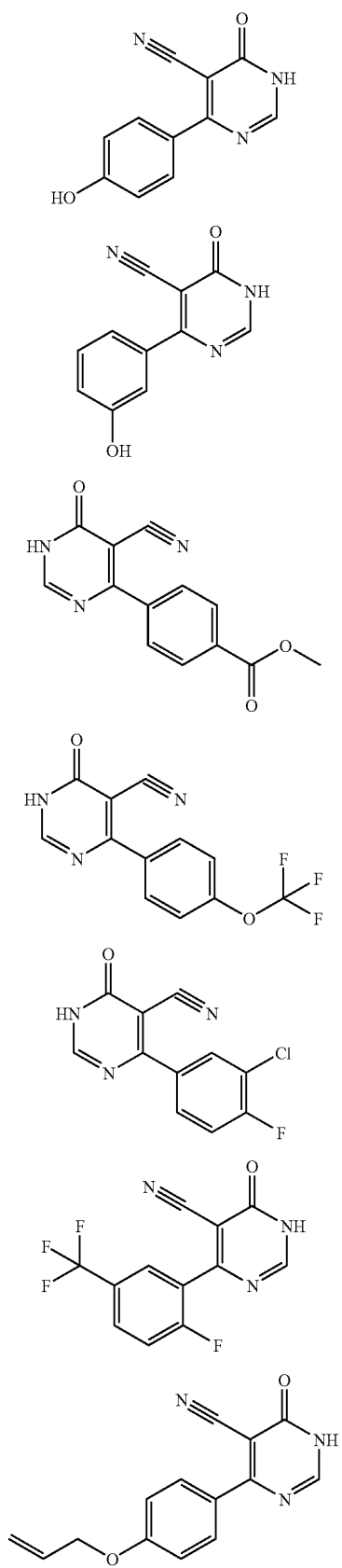
I-38
I-39
I-40
I-41
I-42
I-43
I-44
-continued
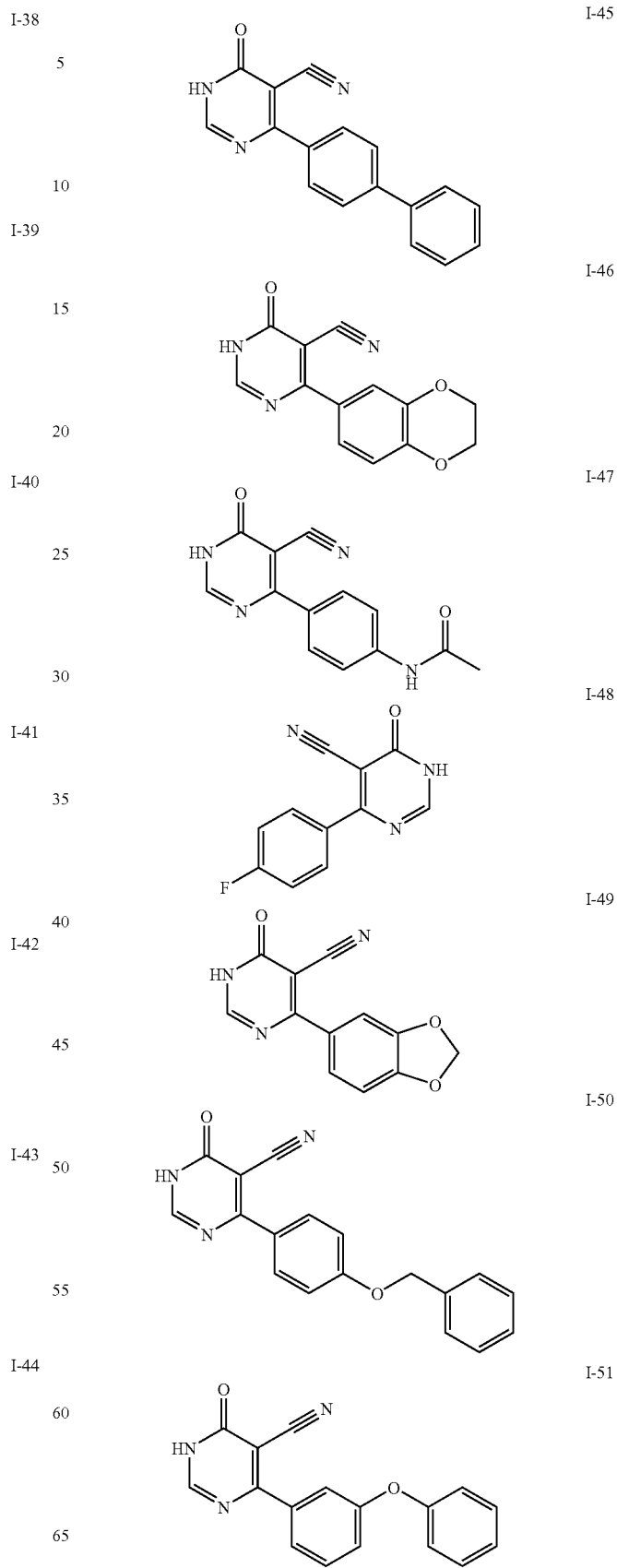
I-45
I-46
I-47
I-48
I-49
I-50
I-51

-continued
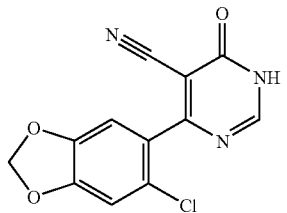
I-52
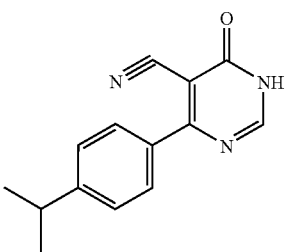
I-53
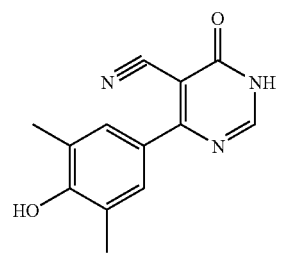
I-54
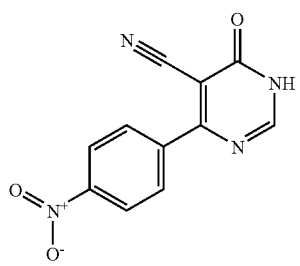
I-55
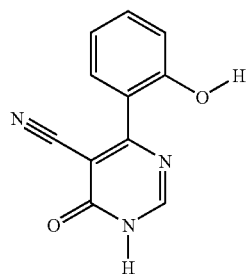
I-56
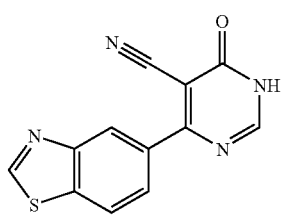
I-57
-continued
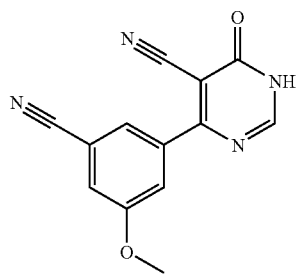
I-58
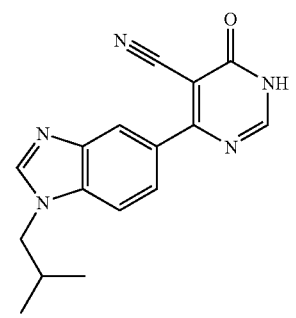
I-59
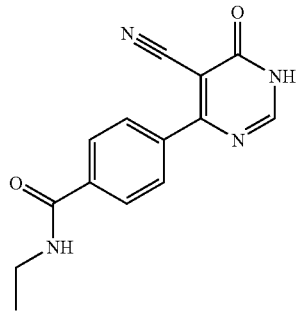
I-60
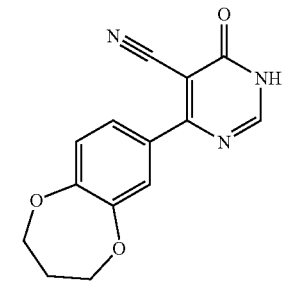
I-61
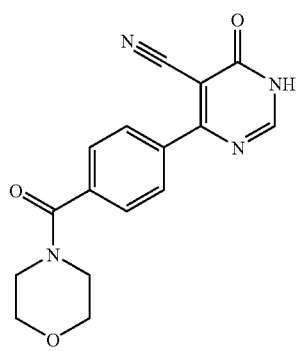
I-62

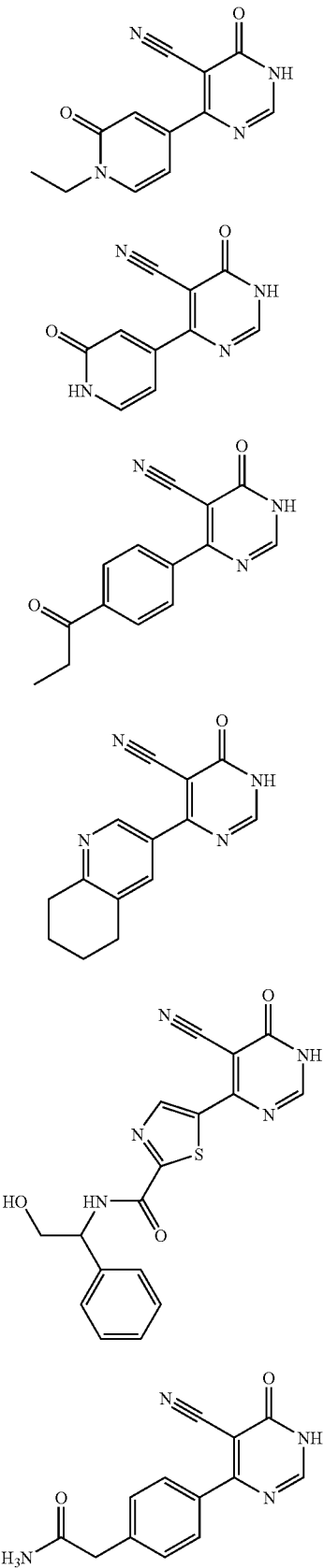

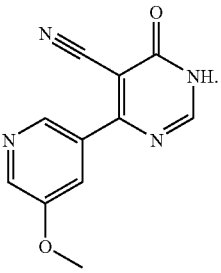

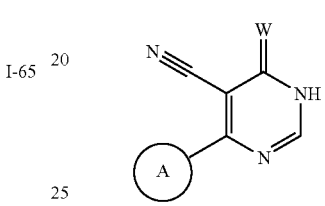

8. A compound of formula I:

or a pharmaceutically acceptable salt thereof, wherein:
W is oxygen or sulfur;
ring A is a 5–6 membered heterocyclyl or heteroaryl ring having 1–4 heteroatoms independently selected from nitrogen, oxygen, or sulfur;
wherein ring A is optionally substituted with 1–4 groups independently selected from halo, —$R^1$, —$OR^1$, —$SR^1$, —$NO_2$, —CN; —$N(R^1)_2$, —$NR^1C(O)R^1$, —$NR^1C(O)N(R^1)_2$, —$NR^1CO_2R^1$, —$NR^1NR^1C(O)R^1$, —$NR^1NR^1C(O)N(R^1)_2$, —$NR^1NR^1CO_2R^1$, —$C(O)C(O)R^1$, —$C(O)CH_2C(O)R^1$, —$NR^1SO_2N(R^1)_2$, —$C(=S)N(R^1)_2$, —$C(=NH)—N(R^1)_2$, =O, =S, =$NNHR^1$, =$NN(R^1)_2$, =$NNHC(O)R^1$, =$NNRCO_2(R^1)$, =$NNHSO_2(R^1)$, or =$NR^1$, wherein two independent occurrences of $R^1$, on the same substituent or different substituents, optionally taken together with the atom or atoms to which each $R^1$ group is bound, form a 3–8 membered cycloalkyl, heterocyclyl, aryl, or heteroaryl ring having 0–3 heteroatoms independently selected from nitrogen, oxygen, or sulfur;
each $R^1$ is independently selected from hydrogen, aliphatic, aryl, heteroaryl or heterocyclyl, wherein each member of $R^1$ except hydrogen is optionally substituted with halo, —$R^2$, —$OR^2$, —$SR^2$, —$NO_2$, —CN, —$N(R^2)_2$, —$NR^2C(O)R^2$, —$NR^2C(O)N(R^2)_2$, —$NR^2CO_2R^2$, —$NR^2NR^2C(O)R^2$, —$NR^2NR^2C(O)N(R^2)_2$, —$NR^2NR^2CO_2R^2$, —$C(O)C(O)R^2$, —$C(O)CH_2C(O)R^2$, —$CO_2R^2$, —$C(O)R^2$, —$C(O)N(R^2)_2$, —$OC(O)N(R^2)_2$, —$S(O)_2R^2$, —$SO_2N(R^2)_2$, —$S(O)R^2$, —$NR^2SO_2R^2$, —$NR^2SO_2N(R^2)_2$, —$C(=S)N(R^2)_2$, —$C(=NH)—N(R^2)_2$, =O, =S, =$NNHR^2$, =$NN(R^2)_2$, =$NNHC(O)R^2$, =$NNHCO_2(R^2)$, =$NNHSO_2(R^2)$, or =$NR^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur;

each R² is independently selected from hydrogen, aliphatic, aryl, heteroaryl or heterocyclyl, wherein each member of R² except hydrogen is optionally substituted with halo, —R³, —OR³, —SR³, —NO₂, —CN, —N(R³)₂, —NR³C(O)R³, —NR³C(O)N(R³)₂, —NR³CO₂R³, —NR³NR³C(O)R³, —NR³NR³C(O)N(R³)₂, —NR³NR³CO₂R³, —C(O)C(O)R³, —C(O)CH₂C(O)R³, —CO₂R³, —C(O)R³, —C(O)N(R³)₂, —OC(O)N(R³)₂, —S(O)₂R³, —SO₂N(R³)₂, —S(O)R³, —NR³SO₂R³, —NR³SO₂N(R³)₂, —C(=S)N(R³)₂, —C(=NH)—N(R³)₂, =O, =S, =NNHR³, =NN(R³)₂, =NNHC(O)R³, =NNHCO₂(R³), =NNHSO₂(R³), or =NR³; and each R³ is independently hydrogen or unsubstituted aliphatic.

9. The compound of claim 8, wherein ring A is a 5–6 membered heterocyclyl or heteroaryl ring having 1–2 heteroatoms independently selected from N, O or S, wherein ring A is optionally substituted with 1–4 groups independently selected from halo, —R¹, —OR¹, —SR¹, —NO₂, —CN, —N(R¹)₂, —NR¹C(O)R¹, —CO₂R¹, —C(O)R¹, —C(O)N(R¹)₂, —S(O)₂R¹, —SO₂N(R¹)₂, —NR¹SO₂R¹, or —C(=S)N(R¹)₂, wherein two independent occurrences of R¹, on the same substituent or different substituents, optionally taken together with the atom or atoms to which each R¹ group is bound, form a 5–7-membered cycloalkyl, heterocyclyl, aryl, or heteroaryl ring having 0–2 heteroatoms independently selected from N, O or S.

10. The compound of claim 8, wherein ring A is pyridinonyl, tetrahydro-quinolinyl, pyridyl, or thiazolyl, wherein each member of ring A is optionally substituted with halo, R², —OR², —SR², —NO₂, —CN, —N(R²)₂, —NR²C(O)R², —CO₂R², —C(O)R², —C(O)N(R²)₂, —S(O)₂R², —SO₂N(R²)₂, —NR²SO₂R², or —C(=S)N(R²)₂.

11. A compound of formula I:

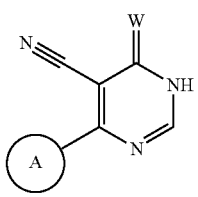

or a pharmaceutically acceptable salt thereof, wherein:
W is oxygen or sulfur; and
ring A is selected from:

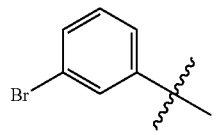
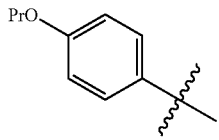
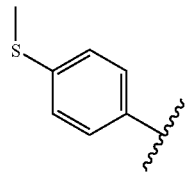
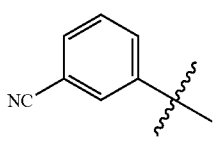
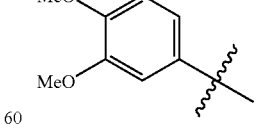
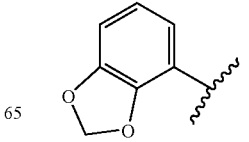
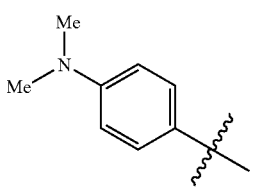
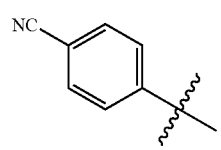

-continued

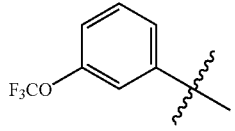
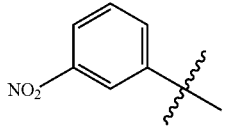
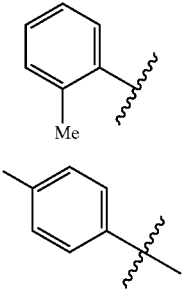
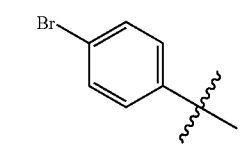
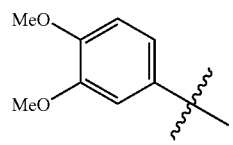
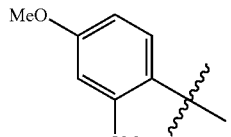
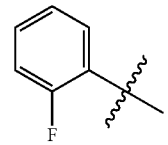
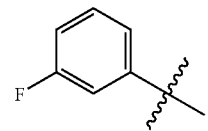
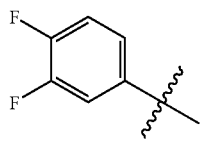
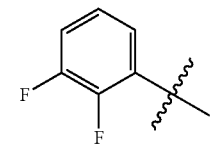
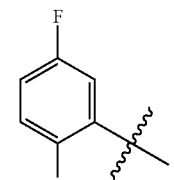
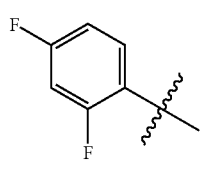
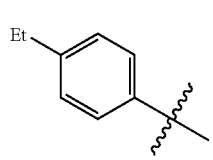
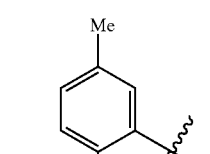

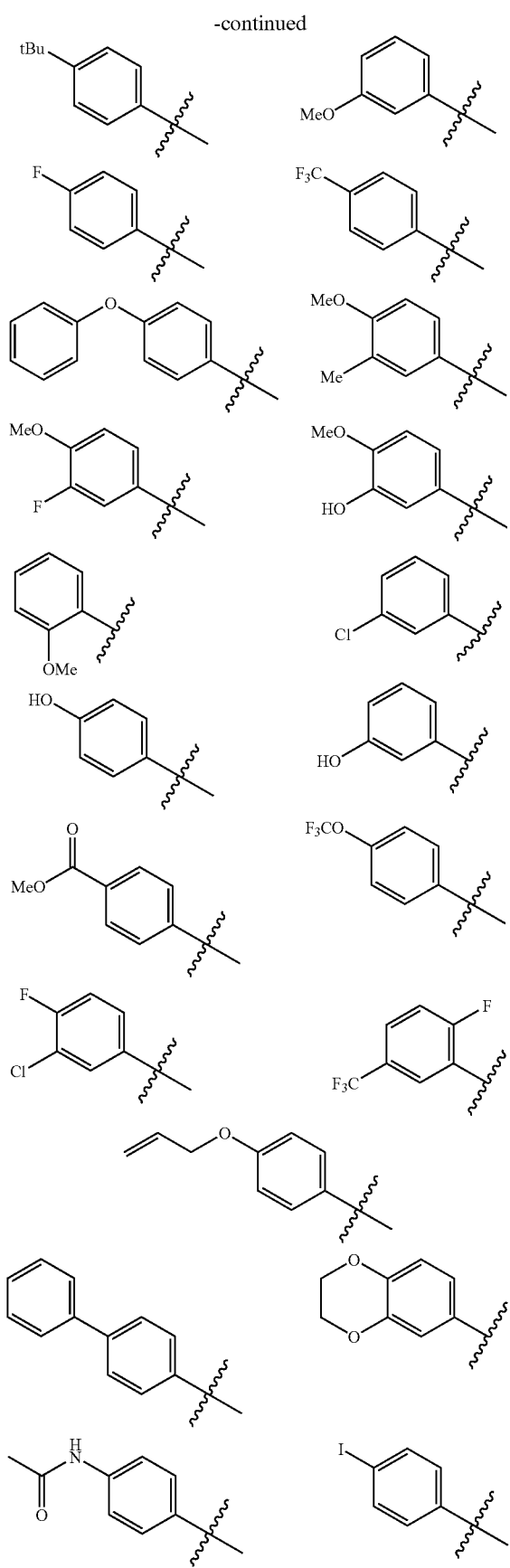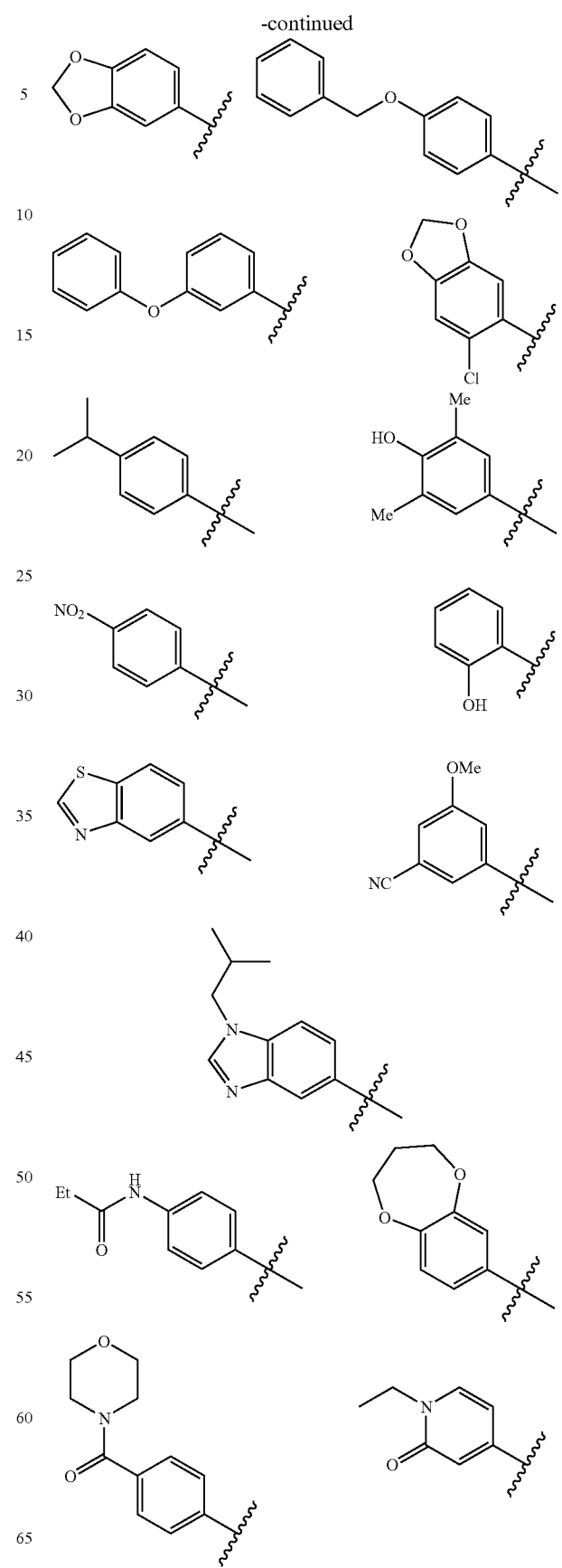

-continued

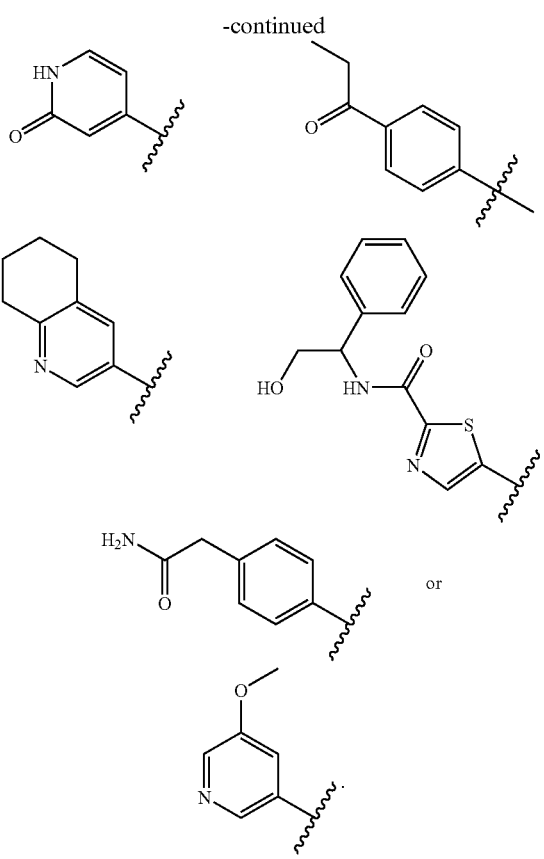

12. A composition comprising a compound of claim 1, 6, 7, 8 or 11, and a pharmaceutically acceptable carrier, adjuvant, or vehicle.

13. The composition of claim 12, additionally comprising an agent for treating diabetes.

14. A method of treating or lessening the severity of diabetes in a patient, comprising administering to said patient a compound of formula I:

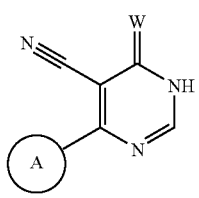

I or a pharmaceutically acceptable salt thereof, wherein:
W is oxygen or sulfur;
ring A is a 5–6 membered aryl, heterocyclyl or heteroaryl ring having 0–4 heteroatoms independently selected from nitrogen, oxygen, or sulfur;
wherein ring A is optionally substitute, with 1–4 groups independently selected from halo, —$R^1$, —$OR^1$, —$SR^1$, —$NO_2$, —CN, —$N(R^1)_2$, —$NR^1C(O)R^1$, —$NR^1C(O)N(R^1)_2$, —$NR^1CO_2R^1$, —$NR^1NR^1C(O)R^1$, —$NR^1NR^1C(O)N(R^1)_2$, —$NR^1NR^1CO_2R^1$, —C(O)C(O)$R^1$, —C(O)CH$^2$C(O)$R^1$, —CO$^2R^1$, —C(O)$R^1$, —C(O)N($R^1$)$_2$, —OC(O)N($R^1$)$_2$, —S(O)$_2R^1$, —SO$_2$N($R^1$)$_2$, —S(O)$R^1$, —$NR^1SO_2R^1$,
—$NR^1SO_2N(R^1)_2$, —C(=S)N($R^1$)$_2$, —C(=NH)—N($R^1$)$_2$, =O, =S, =NNH$R^1$, =NN($R^1$)$_2$, =NNHC(O)$R^1$, =NNHCO$_2$($R^1$), =NNHSO$_2$($R^1$), or =N$R^1$, wherein two independent occurrences of $R^1$, on the same substituent or different substituents, optionally taken together with the atom or atoms to which each $R^1$ group is bound, form a 3–8-membered cycloalkyl, heterocyclyl, aryl, or heteroaryl ring having 0–3 heteroatoms independently selected from nitrogen, oxygen, or sulfur;

each $R^1$ is independently selected from hydrogen, aliphatic, aryl, heteroaryl or heterocyclyl, wherein each member of $R^1$ except hydrogen is optionally substituted with halo, —$R^2$, —$OR^2$, —$SR^2$, —$NO_2$, —CN, —$N(R^2)_2$, —$NR^2C(O)R^2$, —$NR^2C(O)N(R^2)_2$, —$NR^2CO_2R^2$, —$NR^2NR^2C(O)R^2$, —$NR^2NR^2C(O)N(R^2)_2$, —$NR^2NR^2CO_2R^2$, —C(O)C(O)$R^2$, —C(O)CH$_2$C(O)$R^2$, —CO$_2R^2$, —C(O)$R^2$, —C(O)N($R^2$, —OC(O)N($R^2$)$_2$, —S(O)$_2R^2$, —SO$_2$N($R^2$)$_2$, —S(O)$R^2$, —NR SO$_2R^2$, —$NR^2SO_2N(R^2)_2$, —C(=S)N($R^2$)$_2$, —C(=NH)—N($R^2$) =O, =S, =NN($R^2$)$_2$, =NNHC(O)$R^2$, =NNHCO$_2$($R^2$), =NNHSO$_2$($R^2$), or =N$R^2$, wherein two independent occurrences of $R^2$, on the same substituent or different substituents, optionally taken together with the atom or atoms to which each $R^2$ group is bound, form a 3–8-membered cycloalkyl, heterocyclyl, aryl, or heteroaryl ring having 0–3 heteroatoms independently selected from nitrogen, oxygen, or sulfur;

each $R^2$ is independently selected from hydrogen, aliphatic, aryl, heteroaryl or heterocyclyl, wherein each member of $R^2$ except hydrogen is optionally substituted with halo, —$R^3$, —$OR^3$, —$SR^3$, —$NO_2$, —CN, —$N(R^3)_2$, —$NR^3C(O)R^3$, —$NR^3C(O)N(R^3)_2$, —$NR^3CO_2R^3$, —$NR^3NR^3C(O)R^3$, —$NR^3NR^3C(O)N(R^3)_2$, —$NR^3NR^3CO^2R^3$, —C(O)C(O)$R^3$, —C(O)CH$_2$C(O)$R^3$, —CO$^2R^3$, —C(O)$R^3$, —C(O)N($R^3$)$_2$, —OC(O)N($R^3$)$_2$, —S(O)$_2R^3$, —SO$_2$N($R^3$)$_2$, —S(O)$R^3$, —$NR^3SO_2R^3$, —$NR^3SO_2N(R^3)_2$, —C(=S)N($R^3$)$_2$, —C(=NH)—N($R^3$)$_2$, =O, =S, =NNH$R^3$, =NN($R^3$)$_2$, =NNHC(O)$R^3$, =NNHCO$_2$($R^3$), =NNHSO$_2$($R^3$), or =N$R^3$; and each $R^3$ is independently hydrogen or unsubstituted aliphatic; or
a pharmaceutical composition comprising said compound and a pharmaceutically acceptable carrier, adjuvant, or vehicle;
in an amount effective to treat or lessen the severity of diabetes in said patient.

15. The method according to claim 14, wherein said method comprises administering to said patient compound I-1:

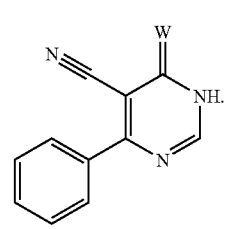

I-1 or a compound selected from:

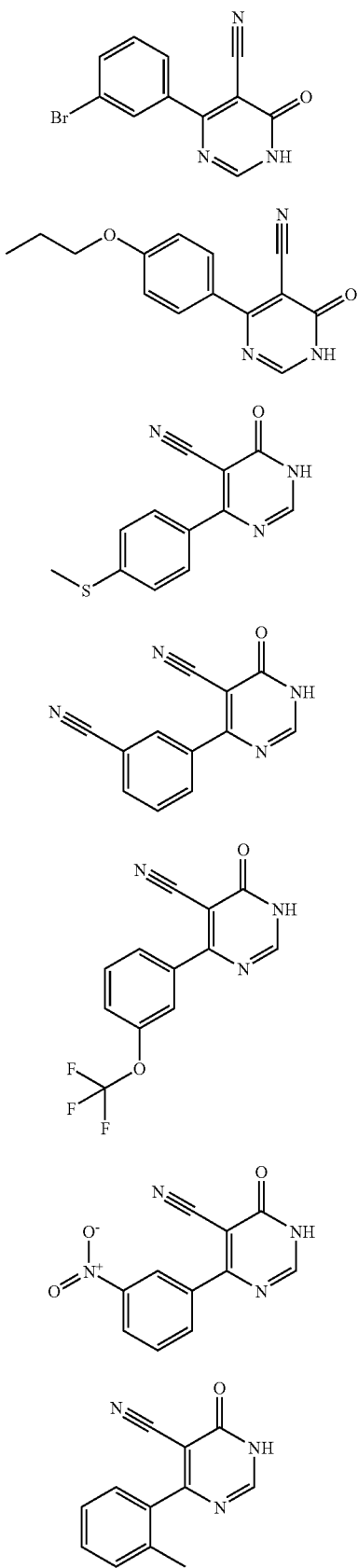
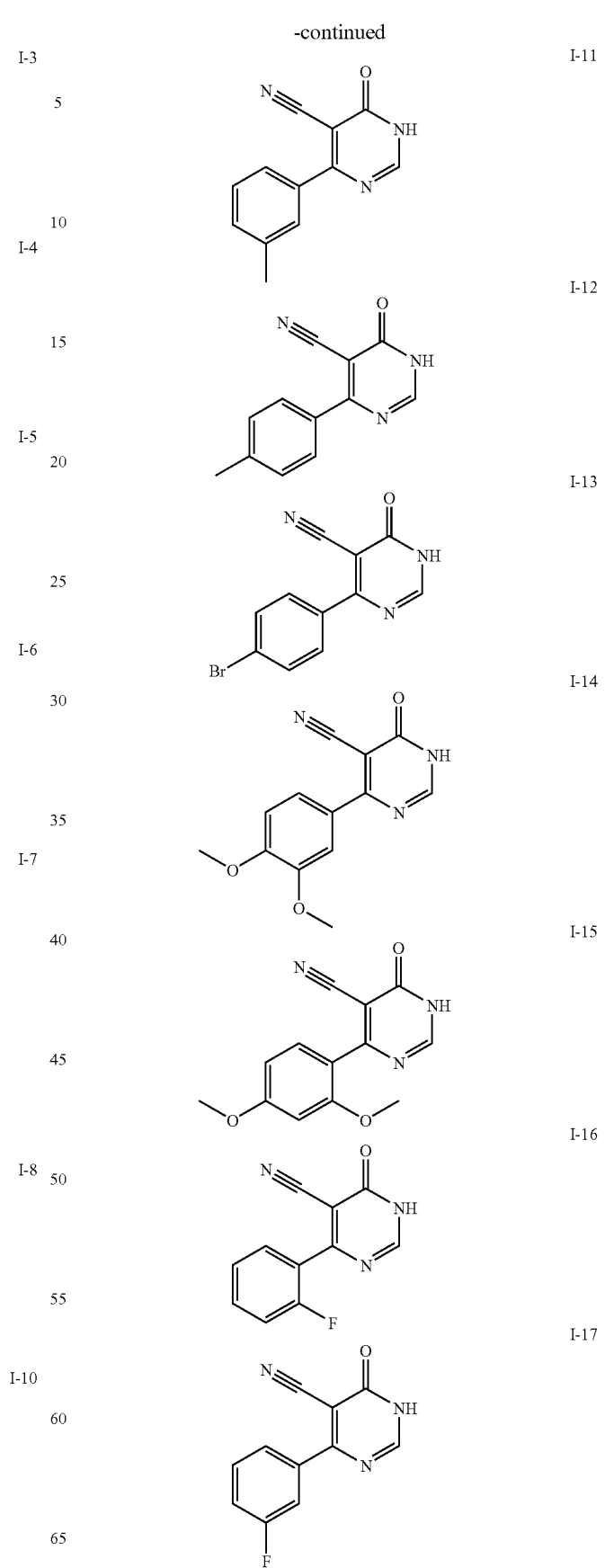

-continued
I-18
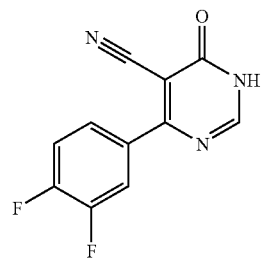
I-19
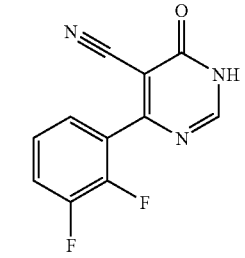
I-20
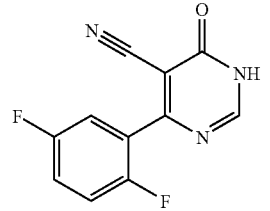
I-21
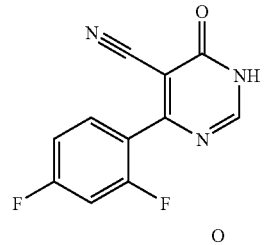
I-22
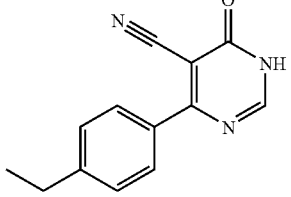
I-23
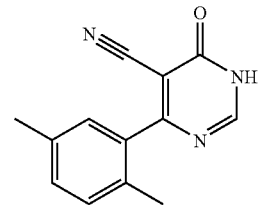
I-24
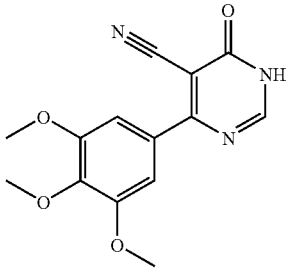
-continued
I-25
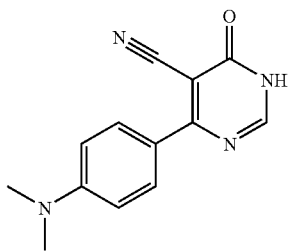
I-26
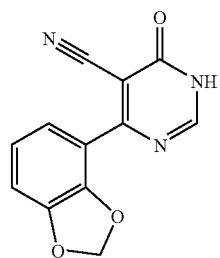
I-27
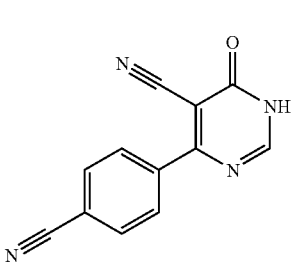
I-28
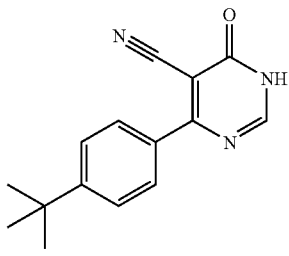
I-29
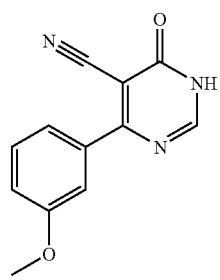
I-30
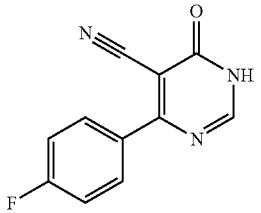

-continued

I-31, I-32, I-33, I-34, I-35, I-36, I-37, I-38, I-39, I-40, I-41, I-42, I-43

-continued
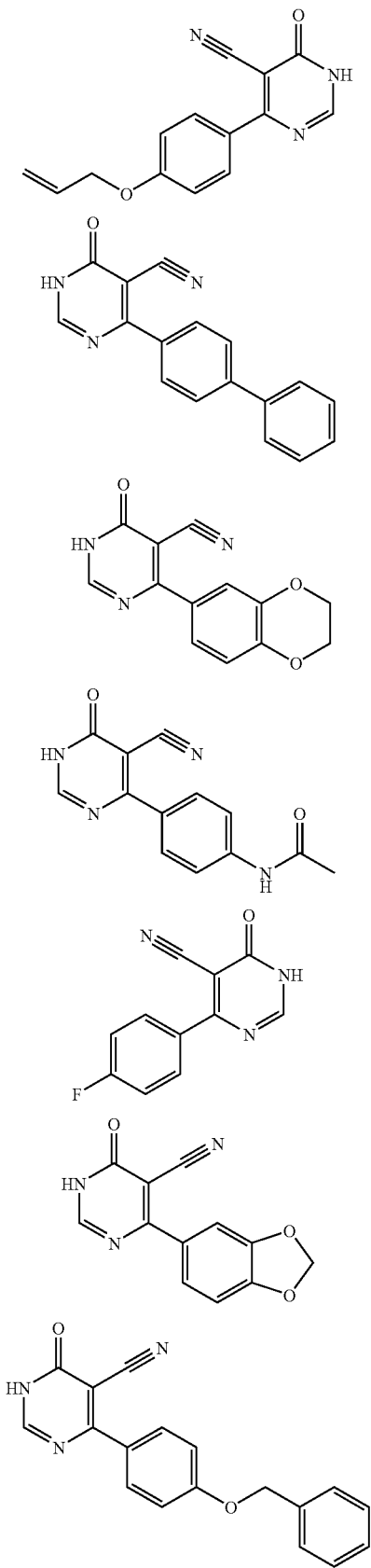
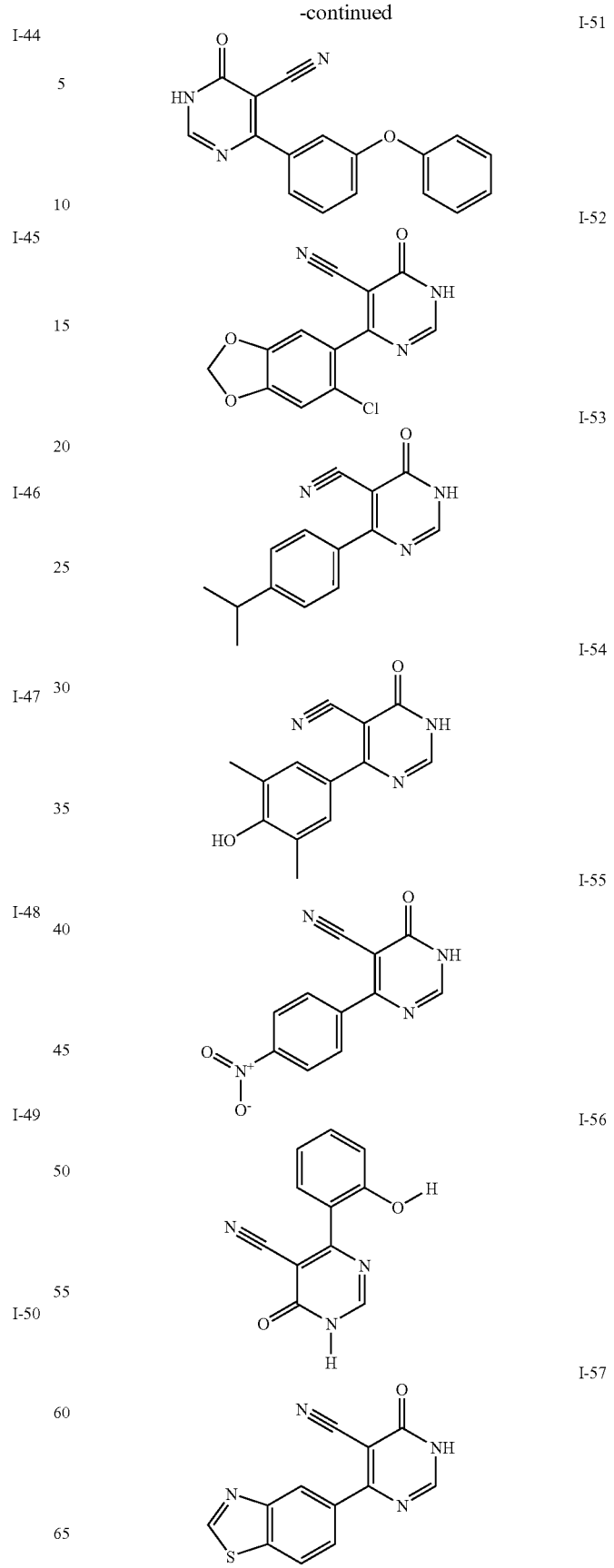

-continued
I-58
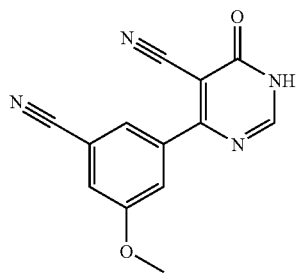
I-59
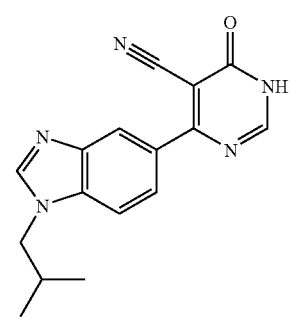
I-60
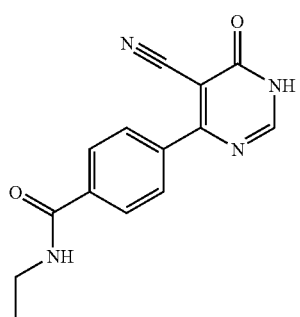
I-61
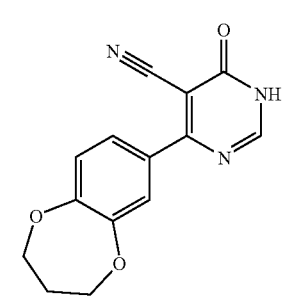
I-62
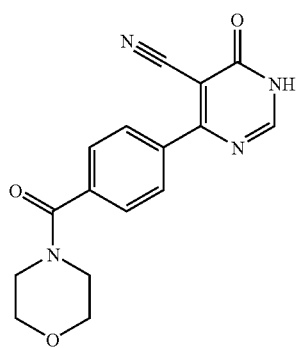
-continued
I-63
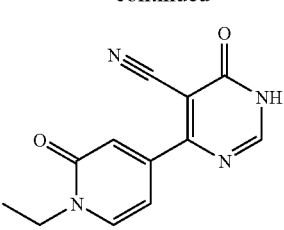
I-64
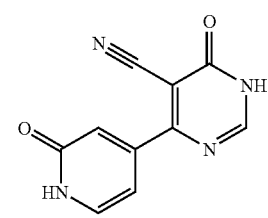
I-65
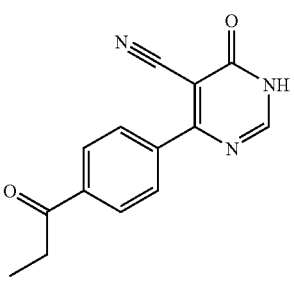
I-66
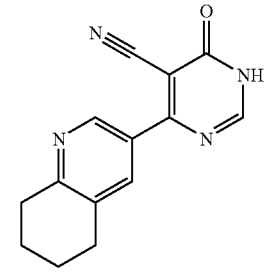
I-67
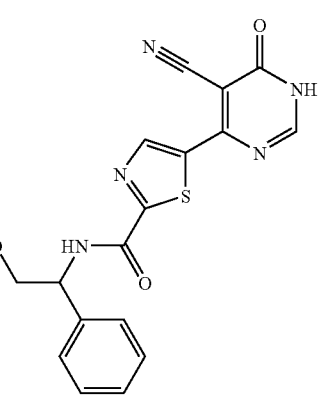
I-68
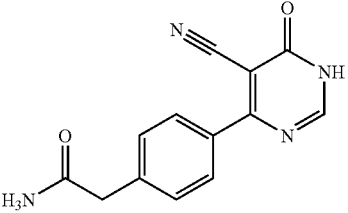

-continued

I-69

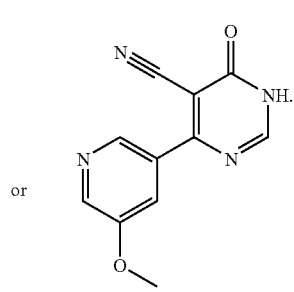

or a pharmaceutical composition comprising said compound and a pharmaceutically acceptable carrier, adjuvant, or vehicle.

16. The method according to claim 15, comprising the additional step of administering to said patient an additional therapeutic agent for treating diabetes, wherein:
said additional therapeutic agent is administered together with said composition as a single dosage form or separately from said composition as part of a multiple dosage form.

17. The method according to claim 14, comprising the additional step of administering to said patient an additional therapeutic agent for treating diabetes, wherein:
said additional therapeutic agent is administered together with said composition as a single dosage form or separately from said composition as part of a multiple dosage form.

18. A method of treating or lessening the severity of stroke in a patient, comprising administering to said patient a compound of formula I:

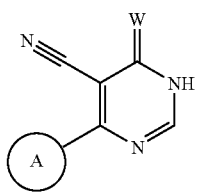

I or a pharmaceutically acceptable salt thereof, wherein:
W is oxygen or sulfur;
ring A is a 5–6 membered aryl, heterocyclyl or heteroaryl ring having 0–4 heteroatoms independently selected from nitrogen, oxygen, or sulfur;
wherein ring A is optionally substitute with 1–4 groups independently selected from halo, —R$^1$, —OR$^1$, —SR$^1$, —NO$_2$, —CN, —N(R$^1$)$_2$, —NR$^1$C(O)R$^1$, —NR$^1$C(O)N(R$^1$)$_2$, —NR$^1$CO$_2$R$^1$, —NR$^1$NR$^1$C(O)R$^1$, —NR$^1$NR$^1$C(O)N(R$^1$)$_2$, —NR$^1$NR$^1$CO$_2$R$^1$, —C(O)C(O)R$^1$, —C(O)CH$_2$C(O)R$^1$, —CO$_2$, —C(O)R$^1$, —C(O)N(R$^1$)$_2$, —OC(O)N(R$^1$)$_2$, —S(O)$_2$R$^1$, —SO$_2$N(R$^1$)$_2$, —S(O)R$^1$, —NR$^1$SO$_2$R$^1$, —NR$^1$SO$_2$N(R$^1$)$_2$, —C(=S)N(R$^1$)$_2$, —C(=NH)—N(R$^2$)$_2$, =O, =S, =NNHR$^1$, =NN(R$^2$)$_2$, =NNHC(O)R$^2$, =NNHCO$_2$(R$^2$), =NNHSO$_2$(R$^2$), or =NR$^2$, wherein two independent occurrences of R$^1$, on the same substituent or different substituents, optionally taken together with the atom or atoms to which each R$^1$ group is bound, form a $^{3-8}$-membered cycloalkyl, heterocyclyl, aryl, or heteroaryl ring having 0–3 heteroatoms independently selected from nitrogen, oxygen, or sulfur;

each R$^1$ is independently selected from hydrogen, aliphatic, aryl, heteroaryl or heterocyclyl, wherein each member of R$^1$ except hydrogen is optionally substituted with halo, —R$^2$, —OR$^2$, —SR$^2$, —NO$_2$, —CN, —N(R$^2$)$_2$, —NR$^2$C(O))R$^2$, —NR$^2$C(O)N(R$^2$)$_2$, —NR$^2$CO$_2$R$^2$, —NR$^2$NR$^2$C(O)R$^2$, —NR$^2$NR$^2$C(O)N(R$^2$)$_2$, —NR$^2$, NR$^2$CO$_2$R$^2$, —C(O)C(O)R$^2$, —C(O)CH$_2$C(O)R$^2$, —CO$^2$R , —C(O)R , —C(O)N(R$^2$)$_2$, —OC(O)N(R$^2$)$_2$, —S(O)$_2$R$^2$, —SO$_2$N(R$^2$)$_2$, —S(O)R$^2$, —NR$^2$SO$_2$R$^2$, —NR$^2$SO$_2$N(R$^2$)$_2$, —C(=S)N(R$^2$)$_2$, —C(=NH)—N(R$^2$)$_2$, =O, =S, =NNHR$^2$, =NN(R$^2$)$_2$, =NNHC(O)R$^2$, =NNHCO$_2$(R$^2$), =NNHSO$_2$(R$^2$)$_2$, or =NR$^2$, wherein two independent occurrences of R$^2$, on the same substituent or different substituents, optionally taken together with the atom or atoms to which each R$^2$ group is bound, form a $^{3-8}$-membered cycloalkyl, heterocyclyl, aryl, or heteroaryl ring having 0–3 heteroatoms independently selected from nitrogen, oxygen, or sulfur;

each R$^2$ is independently selected from hydrogen, aliphatic, aryl, heteroaryl or heterocyclyl, wherein each member of R$^2$ except hydrogen is optionally substituted with halo, —R$^3$, —OR$^3$, —SR$^3$, —NO$_2$, —CN, —N(R$^3$)$_2$, —NR$^3$C(O)R$^3$, —NR$^3$C(O)N(R$^3$)$_2$, —NR$^3$CO$_2$R$^3$, —NR$^3$NR$^3$C(O)R$^3$, —NR$^3$NR$^3$C(O)N(R$^3$)$_2$, —NR$^3$NR$^3$CO$_2$R$^3$, —C(O)C(O)R$^3$, —C(O)CH$_2$C(O)R$^3$, —CO$_2$R$^3$, —C(O)R$^3$, —C(O)N(R$^3$)$_2$, —OC(O)N(R$^3$)$_2$, —S(O)$_2$R$^3$, —SO$_2$N(R$^3$)$_2$, —S(O)R$^3$, —NR$^3$SO$_2$R$^3$, —NR$^3$SO$^2$N(R$^3$)$_2$, —C(=S)N(R$^3$)$_2$, —C(=NH)—N(R$^3$)$_2$, =O, =S, =NNHR$^3$, =NN(R$^3$)$_2$, =NNHC(O)R$^3$, =NNHCO$_2$(R$^3$), =NNHSO$_2$(R$^3$), or =NR$^3$; and each R$^3$ is independently hydrogen or unsubstituted aliphatic; or a pharmaceutical composition comprising said compound and a pharmaceutically acceptable carrier, adjuvant, or vehicle;

in an amount effective to treat or lessen the severity of stroke in said patient.

19. The method according to claim 18, wherein said method comprises administering to said patient compound I-1:

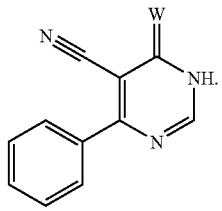

I-1 or a compound selected from:

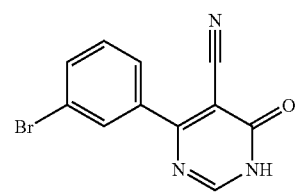

I-3

-continued
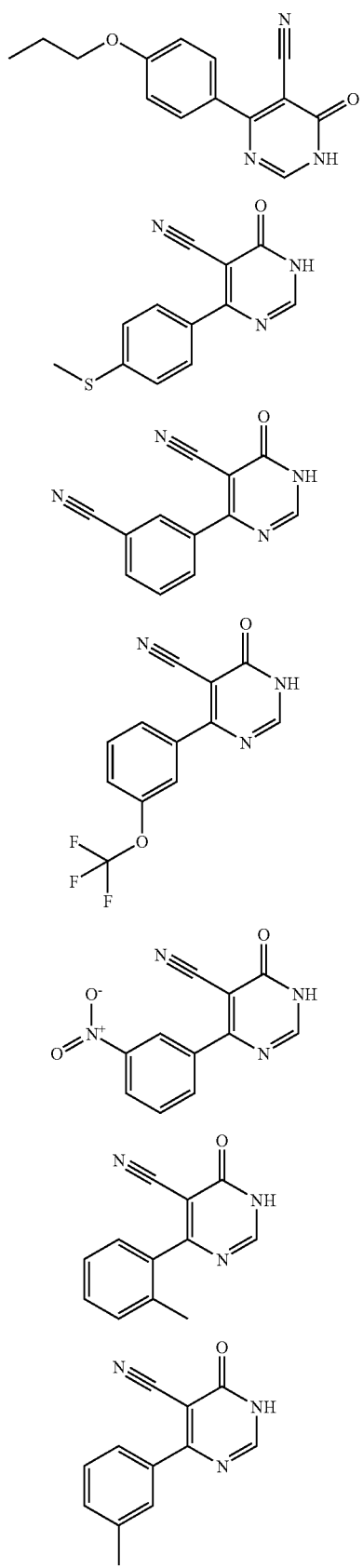
I-4
I-5
I-6
I-7
I-8
I-10
I-11
-continued
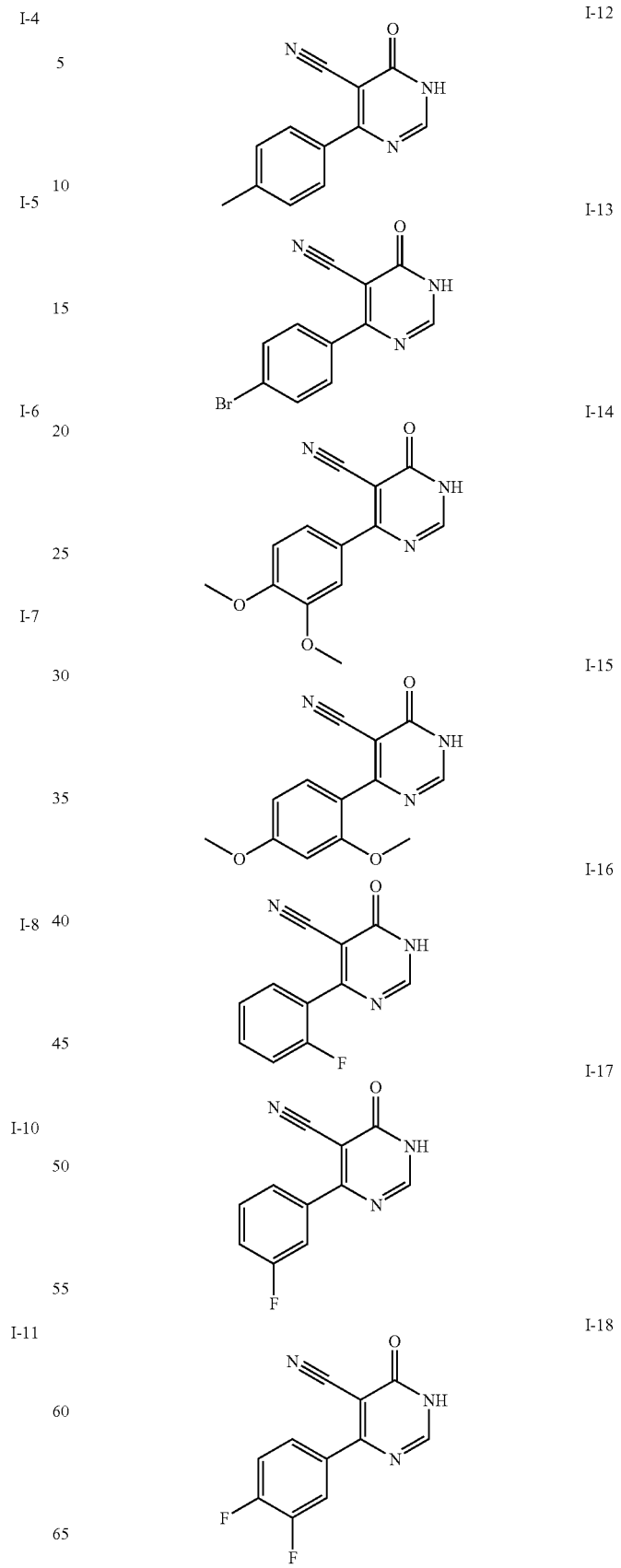
I-12
I-13
I-14
I-15
I-16
I-17
I-18

-continued
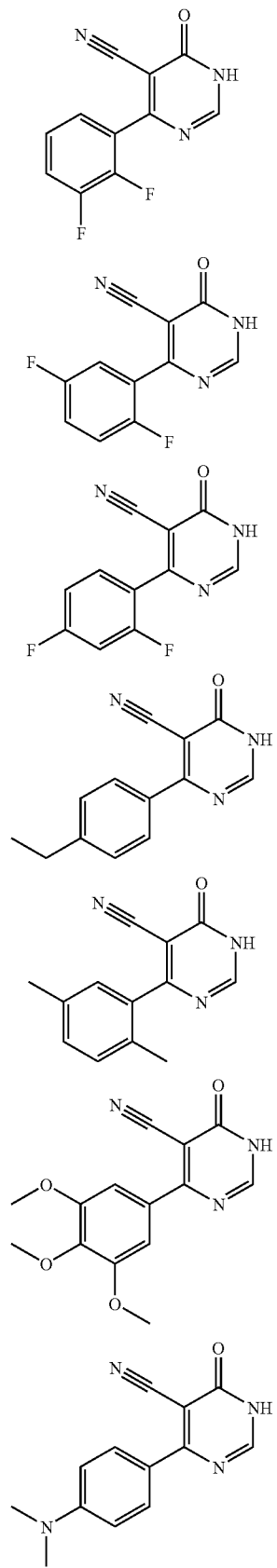
I-19
I-20
I-21
I-22
I-23
I-24
I-25
-continued
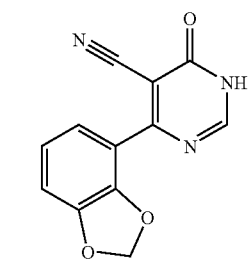
I-26
I-27
I-28
I-29
I-30
I-31

-continued
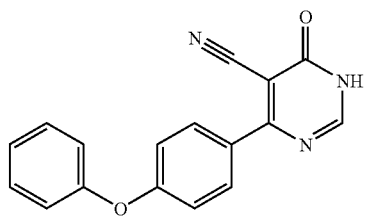
I-32
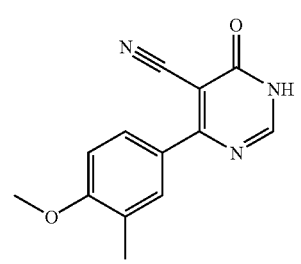
I-33
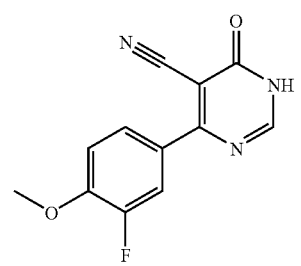
I-34
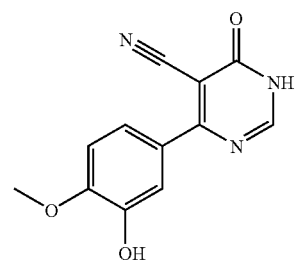
I-35
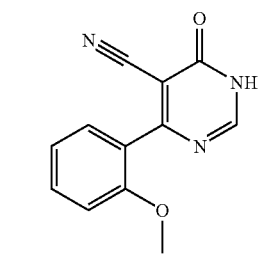
I-36
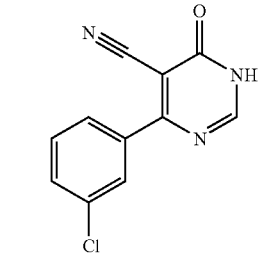
I-37
-continued
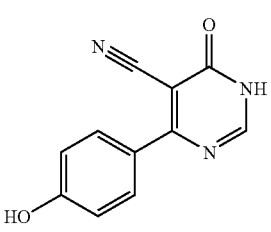
I-38
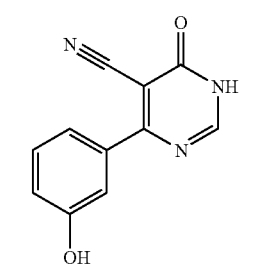
I-39
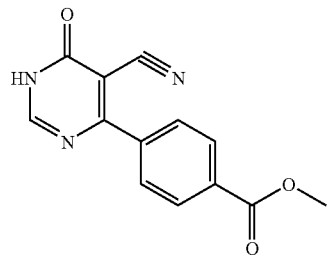
I-40
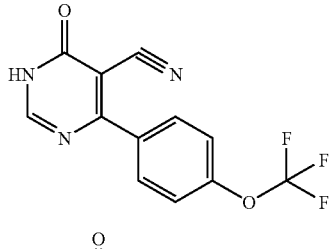
I-41
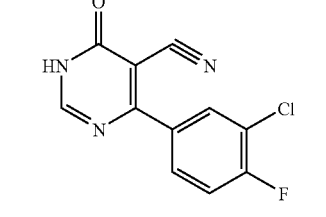
I-42
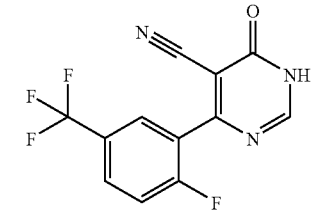
I-43
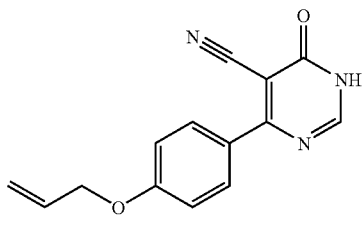
I-44

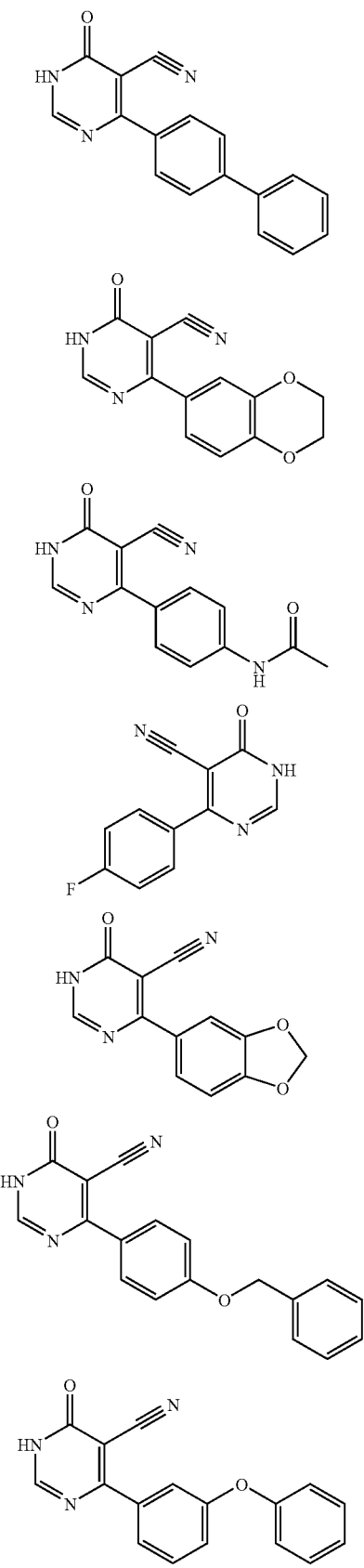

-continued
I-58
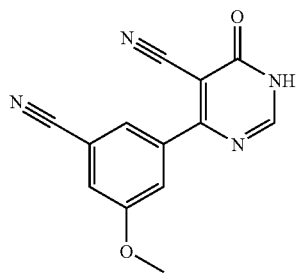
I-59
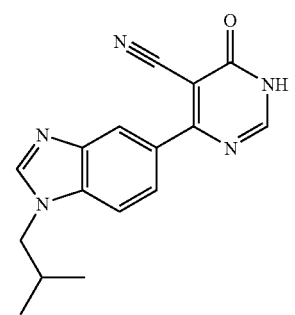
I-60
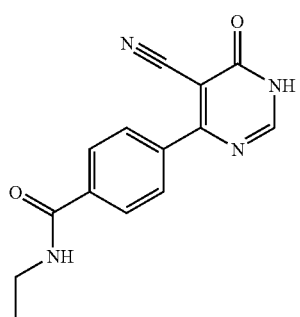
I-61
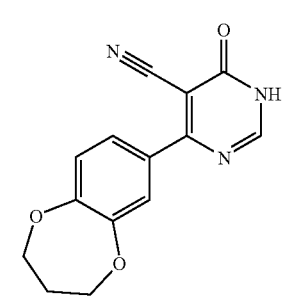
I-62
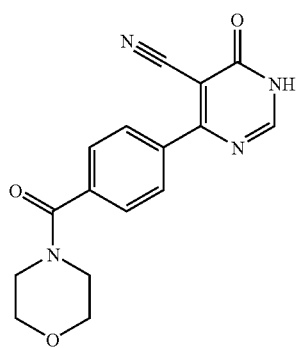
-continued
I-63
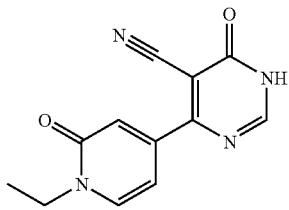
I-64
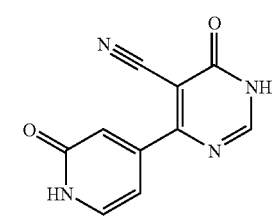
I-65
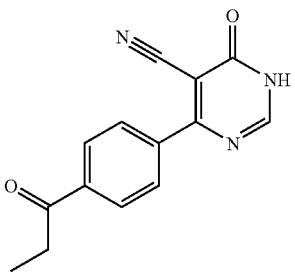
I-66
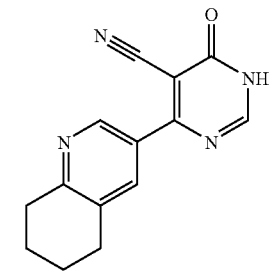
I-67
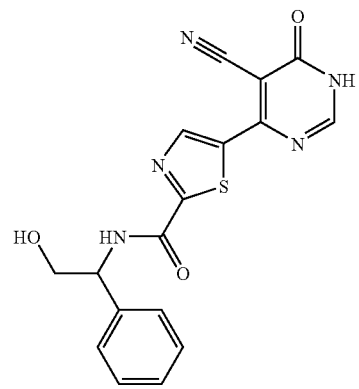
I-68
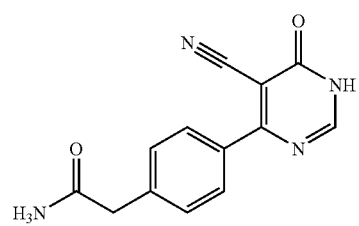

-continued

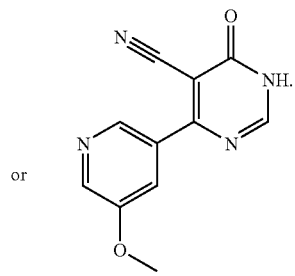

I-69 or a pharmaceutical composition comprising said compound and a pharmaceutically acceptable carrier, adjuvant, or vehicle.

20. The method according to claim 18, comprising the additional step of administering to said patient an additional therapeutic agent for treating stroke, wherein:

said additional therapeutic agent is administered together with said composition as a single dosage form or separately from said composition as part of a multiple dosage form.

21. The method according to claim 19, comprising the additional step of administering to said patient in additional therapeutic agent for treating stroke, wherein:

said additional therapeutic agent is administered together with said composition as a single dosage form or separately from said composition as part of a multiple dosage form.

* * * * *